(12) United States Patent
Feingold et al.

(10) Patent No.: US 9,446,405 B2
(45) Date of Patent: Sep. 20, 2016

(54) MICROFLUIDIC ANALYTE DETECTION CARTRIDGE DEVICE, SYSTEM AND METHOD

(71) Applicants: Joseph Feingold, Wellesley, MA (US); Hector Luis Penagos-Vargas, Cambridge, MA (US)

(72) Inventors: Joseph Feingold, Wellesley, MA (US); Hector Luis Penagos-Vargas, Cambridge, MA (US)

(*) Notice: Subject to any disclaimer, the term of this patent is extended or adjusted under 35 U.S.C. 154(b) by 0 days.

(21) Appl. No.: 14/210,423

(22) Filed: Mar. 13, 2014

(65) Prior Publication Data

US 2014/0273265 A1    Sep. 18, 2014

Related U.S. Application Data

(60) Provisional application No. 61/778,879, filed on Mar. 13, 2013, provisional application No. 61/778,916, filed on Mar. 13, 2013.

(51) Int. Cl.
*G01N 31/16* (2006.01)
*B01L 3/00* (2006.01)
*G01N 27/08* (2006.01)
(Continued)

(52) U.S. Cl.
CPC .... *B01L 3/502776* (2013.01); *B01L 3/502715* (2013.01); *G01N 27/08* (2013.01); *B01L 2200/04* (2013.01); *B01L 2200/143* (2013.01); *B01L 2300/022* (2013.01); *B01L 2300/023* (2013.01); *B01L 2300/0645* (2013.01); *B01L 2300/0663* (2013.01); *B01L 2300/0816* (2013.01); *B01L 2300/0864* (2013.01); *B01L 2300/0867* (2013.01); *B01L 2300/161* (2013.01); *B01L 2300/1822* (2013.01); *B01L 2400/0487* (2013.01); *G01N 21/05* (2013.01); *G01N 21/41* (2013.01); *G01N 21/55* (2013.01); *G01N 2021/0346* (2013.01); *G01N 2021/0353* (2013.01)

(58) Field of Classification Search
None
See application file for complete search history.

(56) References Cited

U.S. PATENT DOCUMENTS 5,641,892 A    6/1997  Larkins et al.
2006/0280655 A1*  12/2006  Gharib ............... B01L 3/50273
                                              422/400
(Continued)

FOREIGN PATENT DOCUMENTS

WO      9800187       1/1998
WO      2009006472 A1  1/2009
WO      2010084268 A1  7/2010

OTHER PUBLICATIONS

Benninger, R.K.P. et al. Fluorescence-Lifetime Imaging of DNA-Dye Interactions within Continuous-Flow Microfluidic Systems, 2007, Angew. Chem. Int. Ed. vol. 46, pp. 2228-2231.*

(Continued)

*Primary Examiner* — Robert Xu
(74) *Attorney, Agent, or Firm* — Cowan, Liebowitz & Latman, P.C.; Steven D. Underwood

(57) ABSTRACT

A microfluidic cartridge for assaying an analyte comprises one or more test channels, each having a lumen; one or more reference solution channels in fluid communication with the test channels; one or more sample channels in fluid communication with the test channels; one or more sensors at least partially exposed in the lumen of the test channels; and a processor coupled to the one or more sensors for measuring properties of the analyte to determine at least one of an identity, concentration, dose, and dosage of the analyte.

6 Claims, 8 Drawing Sheets

(51) Int. Cl.
  *G01N 21/05* (2006.01)
  *G01N 21/41* (2006.01)
  *G01N 21/55* (2014.01)
  *G01N 21/03* (2006.01)

(56) References Cited

U.S. PATENT DOCUMENTS

2010/0305499 A1 12/2010 Matsiev et al.
2012/0065617 A1 3/2012 Matsiev et al.

OTHER PUBLICATIONS

Design and Fabrication of a Microfluidic Electrochemical PH-STAT; by John William Stanton; Submitted in partial fulfillment of the requirements for the degree of Masters of Science; Department of Electrical Enginerring; Case Western Reserve University; May 2010; 86 total pages.

Quantitative Similarity of Zinc and Calcium Binding to Heparin in Excess Salt Solution; J. Matti and Jan C.T. Kwak; Department of Chemistry, Dalhousie University, Halifax, Nova Scotia B3H 4J3, Canada; Jun. 5, 1988; pp. 295-299.

* cited by examiner

Cross-section of photo emitter-detector arrangement for detection of infusion flow (or "drip") rate

MICROFLUIDIC ANALYTE DETECTION CARTRIDGE DEVICE, SYSTEM AND METHOD

CROSS-REFERENCE TO RELATED APPLICATIONS

This application claims priority under 35 U.S.C. 119(e) to U.S. Provisional Patent Application No. 61/778,879, filed Mar. 13, 2013, entitled "Microfluidic Analyte Detection", and to U.S. Provisional Patent Application No. 61/778,916, filed Mar. 13, 2013, entitled "Microfluidic Analyte Detection." The entire contents of each of the above-referenced applications are incorporated herein by reference.

INTRODUCTION

Exemplary embodiments of the microfluidic cartridge device, system and method described herein prevent drug infusion errors. Such errors are known as "never events"—preventable errors that should never occur but nevertheless do occur. An estimated 1.5 m preventable adverse drug events occur each year in the US. More than half of these are caused by IV infusions, which are disproportionately serious and life-threatening. Some errors result from the preparation of a solution of the wrong drug or of the right drug at the wrong concentration. Other errors arise from the incorrect labeling of the contents of an infusion bag. Still other errors occur when the wrong bag is connected to the intravenous line or when the incorrect rate is set on the infusion pump. Beyond the serious risk of patient harm, and potentially irreversible damage to a hospital's reputation, infusion errors also result in significant medical and legal costs, with some estimates on the order of $1 million annually per hospital.

Existing safety precautions involve repetitive staff checks, bar code systems, and/or smart infusion pumps, none of which has effectively addressed the errors described above. Studies have found that even when these safeguards are utilized, drug infusion errors continue to occur. Repetitive checking consumes valuable staff time, is vulnerable to human error, and is often bypassed to save time and hassle. Bar code systems cost the average US hospital ~$500,000 annually, limiting adoption. Cost and integration hurdles are exacerbated by a need for standardization. Adoption of smart pumps has been plagued by high cost and failure to prevent errors. The FDA found that during 2005-2009 at least 56,000 adverse events and 710 deaths were linked to infusion errors that occurred with a smart pump in use.

An exemplary method aspect comprises a method of determining at least one of an identity, concentration, dosage, and dose of an intravenous analyte to be tested prior to being administered to a patient, the method using a microfluidic device comprising a microfluidic sample channel and a microfluidic reference channel in fluid communication with a test microfluidic channel, and a processor. The method comprises: measuring, by the microfluidic device, within the test channel, at least one of electrochemical, chemical, physical, biological, biochemical, thermal and optical properties of the tested analyte in the presence of at least one reference solution; generating, by the processor, a response profile for the tested analyte from the at least one measurement; comparing, by the processor, the generated profile to a known response profile for a specified analyte; estimating, by the processor, a likelihood that the generated profile and known response profile match within an acceptable range; and generating, by the processor, an error signal when the likelihood of a match falls outside the acceptable range.

In various exemplary embodiments, the method comprises: (1) when the likelihood of a match falls outside the acceptable range, administering the analyte to the patient is at least one of prevented, stopped, and adjusted; (2) identifying, by the processor, the tested analyte, based on the at least one measurement; (3) determining, by the processor, a concentration of the tested analyte, based on the at least one measurement; (4) determining, by the processor, a dose of the tested analyte, based on the at least one measurement; (5) determining, by the processor, a dosage of the tested analyte, based on the at least one measurement; (6) analyzing, by the processor, the analyte or the concentration of the analyte for at least one of unsafe drug-drug interactions, conflicts with known characteristics of the patient, quality metrics, hospital treatment guidelines and protocols; and (7) pulsing, by the microfluidic device, the test channel with a predetermined voltage and detecting current elicited to determine at least one of the measurements of the analyte and the reference solution.

An exemplary device aspect comprises a microfluidic device for use in a system comprising an intravenous delivery apparatus in fluid communication with the microfluidic device for providing an injectable test solution containing a test analyte to the microfluidic device, one or more intravenous lines with one or more ports to deliver the injectable test solution to the microfluidic device for analysis, a pump or pressure source to circulate the injectable test solution from one or more intravenous lines, and a reference solution, a valve in each of the intravenous lines for regulating flow of the injectable solution, and one or more controllers for operating the valves. The microfluidic device comprises: one or more test channels, each having a lumen; one or more reference solution channels in fluid communication with the one or more test channels; one or more sample channels in fluid communication with the one or more test channels with each sample channel also in fluid communication with the injectable test solution; a detector coupled to a plurality of sensors that are at least partially exposed within the lumen of the one or more test channels, the detector measuring at least one property of the test analyte; one or more ionic reference solution reservoirs in fluid communication with the one or more reference solution channels; and a processor that generates a response profile for the test analyte from the at least one measurement of a property, compares the generated profile to a known response profile for a specified analyte; estimates a likelihood that the generated profile and known response profile match within an acceptable range; and generates, an error signal when the likelihood of a match falls outside the acceptable range.

In various exemplary embodiments, the device comprises: (1) the detector for measuring at least one of electrochemical, chemical, physical, biological, biochemical, thermal and optical properties of the test analyte; (2) when the processor outputs the error signal to the one or more controllers, the valve controlling flow of the injectable test solution is closed by the one or more controllers; (3) a communication link to an alarm activated by the error signal; (4) information collected by the system by the processor is transmitted via an output interface; and (5) the system further comprising an infusion pump that controls a flow rate of the injectable test solution, and the flow rate is controlled by the processor communicating with the pump, based on the measured properties of the test analyte.

An exemplary method aspect comprises a method of assaying an analyte by a microfluidic device comprising one or more test channels, each having a lumen, one or more reference solution channels in fluid communication with the test channels, one or more sample channels in fluid communication with the test channels, a plurality of electrodes, each electrode at least partially exposed inside the lumen of the test channels and one or more reference solution reservoirs in fluid communication with the reference solution channels. The method comprising: receiving one or more reference solutions into the one or more reference solution channels; receiving one or more samples of a sample solution suspected of containing the analyte into the one or more sample channels; mixing in the test channels the one or more reference solutions and the one or more samples to form a test solution; measuring a response to a stimulus received by a sensor that is located within the test solution; comparing the response to an acceptable range of predetermined values for mixtures of the reference solution and the sample solution; and estimating whether one or more of the identity, concentration, dosage, and dose of the analyte are within the acceptable range based on the comparison.

In various exemplary embodiments, the method comprises: (1) the reference solution comprising at least one of immunoglobulins, water, bio-molecules, antibodies and water soluble ionic salts; (2) applying voltage pulses as the stimulus to the test solution at one or more locations along the test channels and measuring the response to the stimulus received by the sensor comprises measuring current resulting from the voltage pulses; (3) the stimulus is heat present in the test solution and the response is temperature measured at one or more locations along the test channels; (4) the stimulus is at least one or more of hydrogen and hydronium ions in the test solution and the response is a pH measured at one or more locations along the test channels; and (5) applying pulses from at least one or more of a laser, LED, and light source, as the stimuli to the test solution and the sensor comprises one or more photo detectors and the response is measured as at least one of light reflection and refraction.

An exemplary cartridge embodiment comprises a microfluidic cartridge for assaying an analyte. The microfluidic cartridge comprises: one or more test channels, each having a lumen; one or more reference solution channels in fluid communication with the test channels; one or more sample channels in fluid communication with the test channels; one or more sensors at least partially exposed in the lumen of the test channels; and a processor coupled to the one or more sensors for measuring properties of the analyte to determine at least one of an identity, concentration, dose, and dosage of the analyte.

In various exemplary embodiments, the cartridge comprises: (1) the one or more sensors comprising a plurality of electrodes for applying voltage pulses at one or more locations along the test channels and currents between each of the plurality of electrodes are measured by the processor to determine at least one of the identity, concentration, dose, and dosage of the analyte; (2) the one or more sensors comprising at least one thermal sensor for sensing heat at one or more locations along the test channel and the heat sensed by the thermal sensor is used by the processor to measure temperature to determine at least one of the identity, concentration, dose, and dosage of the analyte; (3) the one or more sensors comprising at least one pH sensor for sensing at least one of hydrogen and hydronium ions at one or more locations along the test channel and at least one or more of the hydrogen and hydronium ions sensed by the pH sensor are used by the processor to measure pH to determine at least one of the identity, concentration, dose, and dosage of the analyte; and (4) at least one of a laser, LED, and light source, for applying light pulses at one or more locations along the test channels, the sensor comprising one or more photo detectors for sensing at least one of light reflection and light refraction at one or more locations along the test channels in response to the light pulses, and at least one of the light reflection and light refraction sensed by the one or more photo detectors is used by the processor to determine at least one of the identity, concentration, dose, and dosage of the analyte.

An exemplary method aspect comprises a method of determining at least one of an identity and a concentration of an intravenous analyte to be administered to a patient, the method using a microfluidic device comprising a microfluidic sample channel and a microfluidic reference channel in fluid communication with a test microfluidic channel, and a processor. The method comprises: measuring, by the microfluidic device, within the test channel, at least of electrochemical, chemical, physical, biological, biochemical, thermal or optical properties of the analyte in the presence of at least one reference solution; comparing, by the microfluidic device, the measured properties of the analyte and the reference solution to an acceptable range of predetermined values; determining, by the microfluidic device, whether the measured properties are within the acceptable range of the predetermined values; and generating, by the microfluidic device, an error signal if the measured properties are outside the acceptable range.

In various exemplary embodiments, the method comprises: (1) based on the measured properties of the analyte in the presence of the reference solution, administering of the analyte to the patient is at least one of prevented, stopped, and adjusted based on the error signal generated by the microfluidic device; (2) identifying, by the microfluidic device, the analyte using the measured properties of the analyte; (3) determining, by the microfluidic device, a concentration of the analyte using the measured properties of the analyte; (4) analyzing, by the microfluidic device, the analyte or the concentration of the analyte for at least one of unsafe drug-drug interactions, conflicts with known characteristics of the patient, quality metrics, hospital treatment guidelines and protocols; and (5) pulsing, by the microfluidic device, the test channel with a predetermined voltage and detecting current elicited to determine the measured properties of the analyte and the reference solution.

An exemplary device aspect comprises a microfluidic device for use in a system comprising an intravenous delivery apparatus in fluid communication with the microfluidic device for providing an injectable test solution containing an analyte to the microfluidic device, one or more intravenous lines with one or more ports to deliver the injectable test solution to the microfluidic device for analysis, a pump or pressure source to circulate the injectable test solution from one or more intravenous lines, and a reference solution, a valve in each of the intravenous lines for regulating flow of the injectable solution, and one or more controllers for operating the valves. The microfluidic device comprises: one or more test channels, each having a lumen; one or more reference solution channels in fluid communication with the one or more test channels; one or more sample channels in fluid communication with the one or more test channels with each sample channel also in fluid communication with the injectable test solution; a detector coupled to a plurality of sensors that are at least partially exposed within the lumen of the one or more test channels, the detector for measuring properties of the analyte; one or more ionic reference solution reservoirs in fluid communication with the one or more reference solution channels; and a processor for comparing measured properties of the analyte to an acceptable range of predetermined values, determining whether the measured properties are within the acceptable range, and generating an error signal if the measured properties are outside the acceptable range.

In various exemplary embodiments, the microfluidic device comprises: (1) the detector configured to measure at least one of electrochemical, chemical, physical, biological, biochemical, thermal and optical properties of the injectable test solution; (2) when the processor outputs the error signal to the one or more controllers, the valve is closed by the one or more controllers; (3) the acceptable range of predetermined values and the measured properties corresponding to at least one of the measured electrochemical, chemical, physical, biological, biochemical, thermal and optical properties of the analyte, and at least one of an analyte identity, an analyte concentration, an analyte dose, and an analyte dosage are determined by the processor based on the comparison of the measured properties and the acceptable range; (4) an alarm that indicates that the one or more measured properties of the analyte and are outside the acceptable range; (5) information collected by the system from the detector is transmitted via an output interface; the system, further comprising an infusion pump that controls a flow rate of the injectable test solution, and the flow rate is controlled based on the measured properties of the analyte by the processor communicating with the pump; and (6) determining whether the measured properties are within the acceptable range based on a probabilistic estimate of the measured properties.

An exemplary method aspect comprises a method of assaying an analyte by a microfluidic device comprising one or more test channels, each having a lumen, one or more reference solution channels in fluid communication with the test channels, one or more sample channels in fluid communication with the test channels, a plurality of electrodes, each electrode at least partially exposed inside the lumen of the test channels and one or more reference solution reservoirs in fluid communication with the reference solution channels. The method comprises: receiving one or more reference solutions into the one or more reference solution channels; receiving one or more samples of a sample solution suspected of containing the analyte into the one or more sample channels; mixing in the test channels the one or more reference solutions and the one or more samples to form a test solution; measuring a response to a stimulus received by a sensor that is located within the test solution; comparing the response to an acceptable range of predetermined values for mixtures of the reference solution and the sample solution; and estimating whether one or more of the identity, concentration, dosage, and dose of the analyte are within the acceptable range based on the comparison.

In various exemplary embodiments, the method comprises: (1) the reference solution comprising at least one of immunoglobulins, water, bio-molecules, antibodies and water soluble ionic salts; (2) applying voltage pulses as the stimulus to the test solution at one or more locations along the test channels and measuring the response to the stimulus received by the sensor comprises measuring current resulting from the voltage pulses; (3) the stimulus is heat present in the test solution, and the response is temperature measured at one or more locations along the test channels; (4) the stimulus is at least one or more of hydrogen and hydronium ions in the test solution, and the response is a pH measured at one or more locations along the test channels; and (5) applying pulses from at least one or more of a laser, LED, and light source, as the stimuli to the test solution, and the sensor comprising one or more photo detectors and the response is measured as at least one of light reflection and refraction.

An exemplary microfluidic cartridge aspect comprises a microfluidic cartridge for assaying an analyte. The microfluidic cartridge comprises: one or more test channels, each having a lumen; one or more reference solution channels in fluid communication with the test channels; one or more sample channels in fluid communication with the test channels; one or more sensors at least partially exposed in the lumen of the test channels; and a processor coupled to the one or more sensors for measuring properties of the analyte to determine at least one of an identity, concentration, dose and dosage of the analyte.

In various exemplary embodiments, the microfluidic cartridge comprises: (1) the one or more sensors comprising a plurality of electrodes for applying voltage pulses at one or more locations along the test channels and currents between each of the plurality of electrodes are measured by the processor to determine at least one of the identity, concentration, dose and dosage of the analyte; (2) the one or more sensors comprising at least one thermal sensor for sensing heat at one or more locations along the test channel and the heat sensed by the thermal sensor is used by the processor to measure temperature to determine at least one of the identity, concentration, dose and dosage of the analyte; (3) the one or more sensors comprising at least one pH sensor for sensing at least one of hydrogen and hydronium ions at one or more locations along the test channel and at least one or more of the hydrogen and hydronium ions sensed by the pH sensor are used by the processor to measure pH to determine at least one of the identity, concentration, dose and dosage of the analyte; and (4) at least one of a laser, LED, and light source, for applying light pulses at one or more locations along the test channels, wherein the sensor comprises one or more photo detectors for sensing at least one of light reflection and light refraction at one or more locations along the test channels in response to the light pulses, and wherein at least one of the light reflection and light refraction sensed by the one or more photo detectors is used by the processor to determine at least one of the identity, concentration, dose and dosage of the analyte.

An exemplary embodiment comprises a method of discriminating one or more of the identity, concentration, dosage, and dose of an analyte in solution from that of a known target analyte in solution. The method comprises: measuring one or more electrochemical, chemical, physical, biological, biochemical, thermal or optical properties of the tested analyte in the presence of one or more reference solutions, each having one or more known electrochemical, chemical, physical, biological, biochemical, thermal or optical properties; comparing the measured properties to one or more predetermined values for the known analyte solution mixed with the same reference solutions; estimating the likelihood that one or more of the identity, concentration, dosage, and dose of the tested analyte matches that of the known analyte in solution, based on the measured properties of the tested analyte in solution and known properties of the known analyte in solution; reporting whether there is a match or mismatch within a range of acceptable error, e.g., at a particular confidence level; and generating an error signal if a mismatch is detected at a particular confidence level between one or more of the identity, concentration, dosage, and dose of the tested and target analytes in solution.

An exemplary embodiment comprises a microfluidic device for determining an identity and/or a concentration of an intravenous analyte to be administered, or being administered, to a patient. The microfluidic device comprises a microfluidic sample channel and a microfluidic reference channel in fluid communication with a test microfluidic channel; a detector for measuring, within the test channel, at least one or more of electrochemical, chemical, physical, biological, biochemical, thermal or optical properties of the analyte in the presence of at least one reference solution having one or more known electrochemical, chemical, physical, biological, biochemical, thermal or optical properties; a processor within the microfluidic device for comparing the measured properties of the analyte and the reference solution to one or more predetermined values, determining whether the measured properties match the predetermined values of the analyte within a known range and generating an error signal if the measured properties do not match the predetermined values within the known range.

BRIEF DESCRIPTION OF THE DRAWINGS

The objects and features of the invention can be understood more completely by referring to the drawings described below and the accompanying descriptions. The figures are not necessarily to scale, emphasis instead generally being placed upon illustrative principles.

DETAILED DESCRIPTION OF CERTAIN EXEMPLARY EMBODIMENTS

Figure 1:
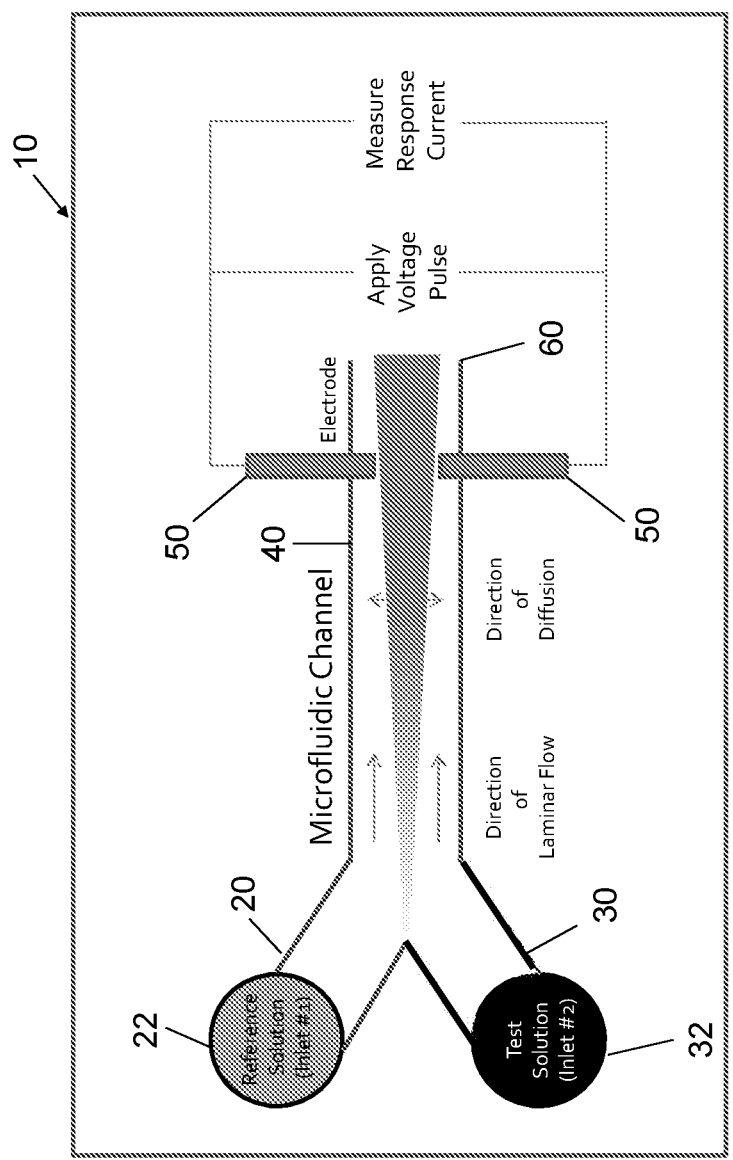
FIG. 1 is a schematic showing an embodiment of a microfluidic cartridge.

Embodiments of the present invention relate in part to microfluidic cartridges, a microfluidic device, a patient safety system using the microfluidic device and methods of using the microfluidic device and the patient safety system, that identify soluble analytes of interest, e.g., drugs, and determine information about the analyte in real time. The microfluidic cartridges and devices compare each of the identity, concentration, dosage, and dose of a tested analyte to the corresponding property, e.g., identity, concentration, dosage, and dose of a known target analyte. As used herein, the term "concentration" refers to volume of drug per unit volume of infusible solution. As used herein, the term "dosage" refers to one of the volume of drug administered per unit time, i.e., milliliters/minute or milliliters/hour, and or the mass of drug administered per unit time, i.e., milligrams/minute or milligrams/hour. As used herein, the term "dose" refers to one of the mass, i.e., in milligrams, and/or the total volume of drug administered.

For example, in some embodiments, detection and measurement are accomplished by measuring an electrochemical profile of the analyte in solution in the presence of a reference solution. The reference solution may have a known or predetermined electrochemical profile and the analyte may be known to bind certain ions. When the analyte solution flows through a microfluidic channel in combination with a reference solution containing ions to which the analyte binds, the number of free ions in the mixed solution will change in proportion to the amount of analyte in the solution. When the number of free ions changes, an electrochemical profile of the mixed solution also changes. As a result, the electrochemical profile of the solution is used as a proxy for determining analyte concentration and identity.

The detection method is not limited to detection and measurement based on the electrochemical properties of the analyte. In some embodiments, an analyte of interest in a test sample is characterized using one or more of electrochemical, immunochemical, biological, biochemical, optical and thermal methods. Individual tests can be run in series or parallel across one or more microfluidic channels in one or more microfluidic cartridges. The results of individual tests can be combined to construct a unique chemical/physical/biological profile of an analyte in a test sample, in order to identify the analyte or determine the analyte's concentration.

In some embodiments, microfluidic cartridges form part of a patient safety system that is used at the bedside, e.g., in a hospital or other clinical healthcare setting, to verify that a patient is about to be given the proper injectable, e.g., intravenous, medication. The patient safety system detects mismatch between one or more of the identity, concentration, dosage, and dose of the intended, e.g., prescribed, drug, and the corresponding value of the drug that is about to be administered. Thus, the patient safety system acts as a gatekeeper or last line of defense between an intravenous delivery apparatus (e.g., bag, syringe, port, or line) and the patient, minimizing the risk of human or other errors that would lead to administering the incorrect drug, or the right drug at the incorrect dosage or dose.

As described herein, exemplary embodiments of the microfluidic cartridge device, system and method reduce and/or prevent human error in the administration of infusible drugs, by interposing an automated gatekeeper between the infusion pump, bag, or line, and the patient's veins. Using microfluidic technology, the microfluidic cartridge device analyzes a sample of the drug before it reaches the patient and determines whether it is the right drug at the right dose. According to an exemplary embodiment, prior to an infusion, a small sample of the intravenous drug solution is diverted to the microfluidic cartridge device, which uses a disposable or reusable cartridge to analyze the identity and concentration of the sample, and tracks the drip rate. Each cartridge includes microfluidic channels, which are configured. Multiple microfluidic-based tests are performed quickly inside a single cartridge, enabling the creation of a detailed physical/chemical profile of the test sample. The resulting profile is then compared to a library of known profiles, i.e. reference profiles, in order to detect and report a match or mismatch between the contents of the test sample and rate of the infused solution and the intended drug at the intended dose. If a mismatch is detected, the microfluidic cartridge device-based system alerts the healthcare staff, and also may directly stop, alter, or prevent the flow of drug to the patient via a mechanical valve or a control signal sent to the infusion pump.

Microfluidic Cartridges

FIG. 1 shows a microfluidic cartridge, in accordance with an exemplary embodiment. In this non-limiting example, microfluidic cartridge 10 includes a reference solution microfluidic channel 20 and a sample microfluidic channel 30 that are in fluid communication with a test microfluidic channel 40. The reference channel 20, sample channel 30 and test channel 40 may have substantially matching cross sections that are typically in the 100-500 $\mu m^2$ range. The reference channel 20 and the sample channel 30 may be approximately 1 cm long, while the test channel 40 may be approximately 2-3 cm in length. The reference solution channel 20 connects the test channel 40 to a reference solution reservoir 22 containing a reference solution. The sample channel 30 introduces a sample solution to be tested into the test channel 40 from an intravenous line (IV) or intravenous bag 32. The reference solution channel 20 and the sample channel 30 communicate with a first, upstream end of the test channel 40. Test sample and reference solution flow into the test channel 40, and the laminar flow of the test channel transports the test and reference solutions to a second, downstream end of the test channel 40 towards one or more electrodes 50. The test channel 40 may comprise a lumen and the electrodes 50 may be at least partially exposed within the lumen of the test channel 40.

The test sample and reference solution mix via diffusion as the two solutions travel down the test channel 40. Electrode(s) 50 are positioned within the mixture as it passes through the test channel 40. Electrodes 50 are attached to a switched voltage source, e.g., such as a switched DC source, and when pulsed have a potential across them. This voltage pulse causes a current to flow between the electrodes 50 proportional to an ionic concentration and a function of the type of ions present. The conductance or response current across the electrodes 50 is measured by a current measuring circuit or an amperage meter. A conductance profile of the fluid traveling along the channel 40 is then generated. Conductivity is assessed by recording the current in response to voltage pulses. Currents can be amplified, digitized and recorded with standard amplifier chips and A/D converter cards. Software can be used to control the delivery of the voltage pulses and to calculate the mean current at different locations along the test channel 40. The mixed solution exits the test channel 40 at exit port 60, into a waste chamber.

The reference solution is a conductive solution, e.g., an ionic or electrolyte solution. In addition, the conductive solution is typically an aqueous solution. By way of non-limiting example, the ionic solution may include $Ag^+$, $Fe^{2+}$, $Fe^{3+}$, $Zn^{2+}$, $Li^+$, $K^+$, $Na^+$, $Rb^+$, $Cs^+$, $Fr^+$, $Be^{2+}$, $Mg^{2+}$, $Ca^{2+}$, $Sr^{2+}$, $Ba^{2+}$, $Ra^{2+}$, and/or $Al^{3+}$. Ionic solutions can be prepared using suitable salts, for example, calcium chloride, magnesium chloride, zinc chloride, potassium phosphate, potassium carbonate, potassium hydroxide, sodium phosphate, sodium hydroxide, iron nitrate, and silver nitrate.

A particular reference solution can be selected depending on the analyte to be detected and its expected concentration. By way of non-limiting example, the reference solution can have a concentration of between about 1 µM and up to several M, depending on the reference solution's maximum solubility. For example, $CaCl_2$ has an upper molar concentration of 5M, whereas the upper concentration of $ZnCl_2$ is 31M. Suitable concentrations of the reference solution include, for example, about 1 µM, 5 µM, 10 µM, 50 µM, 100 µM, 200 µM, 300 µM, 400 µM, 500 µM, 1 mM, 5 mM, 10 mM, 50 mM, 100 mM, 200 mM, 300 mM, 400 mM, 500 mM, 1 M, 2 M, 3 M, 4 M or 5 M. The choice of concentration depends on whether the mix between reference and test solution results in a decrease or increase of free ions. The selected reference concentration should maximize the range of concentrations of test solutions that can be determined. If the reaction between test and reference solutions reduces the number of free ions, it is advantageous to start with a reference solution at the highest possible concentration, i.e., with maximal number of free ions corresponding to maximal ionic conductivity. A low initial reference concentration may decrease the accuracy of detecting the concentration of the test solution because of a low saturation point.

The test sample is any solution that is interrogated for the presence and/or concentration of an analyte of interest, e.g., a drug. For example, the test sample can be a fluid sample from an intravenous bag containing a drug that is to be administered to a patient. In some embodiments, the test sample is prepared by dissolving, suspending, or reconstituting a solid in a solvent such as water. In another embodiment, the test sample can be drawn from the contents of an IV line or from a syringe or other injectable device. None of these examples is meant to limit the method of introducing the test sample into the microfluidic cartridge 10.

Electrochemical reactions between an analyte of interest and free ions in a reference solution can be used to detect the concentration and identity of the analyte. Any analyte, such as a drug of interest, that binds one or more ions can be identified and measured using the systems and methods of the invention, such as, for example, anticoagulants, e.g., heparin, narcotics, e.g., morphine, and anesthetics, e.g., propofol, insulin, and electrolytes, e.g., potassium chloride (KCl). The drug of interest typically is present in a test solution, e.g., an injectable IV solution. A test solution suspected of containing the drug of interest is paired with one or more reference solutions, each containing an ion to which the drug of interest is known to bind with a specific affinity. Based on this pairing, the concentration of a test solution drawn from a drug with a presumed identity can be determined using the microfluidic cartridge 10 described herein.

For example, since insulin is known to bind zinc, the insulin content of a solution, e.g., an IV solution, can be confirmed by mixing in a microfluidic channel the insulin-containing test solution together with an aqueous zinc chloride reference solution. Similarly, since heparin also is known to bind zinc, the heparin content of a solution, e.g., an IV solution, can also be confirmed by mixing in the microfluidic test channel 40 a heparin-containing test solution together with an aqueous zinc chloride reference solution. Insulin and heparin bind free zinc ions, thereby decreasing the zinc ion concentration of the mixture. The current in response to a voltage pulse in the test channel 40 is proportional to the concentration of free ions left in the mixture. The current, or change in current from a baseline measurement, can provide an estimate of the original concentration of the test solution, e.g., insulin or heparin.

Different drugs can be distinguished by testing drug-containing solutions with multiple reference solutions. For example, the identity and concentration of heparin and insulin saline solutions can be discriminated using aqueous reference solutions of calcium chloride, magnesium chloride, and/or zinc chloride. As shown in Table 1, a comparison of binding constants to heparin is provided indicating that calcium and zinc exhibit similar binding properties to heparin, which is greater than that exhibited by magnesium. Mattai J., Kwak J. C. "Quantitative similarity of zinc and calcium binding to heparin in excess salt solution." *Biophys. Chem.* 1988; 31: 295-299.

TABLE 1

| Ionic concentration (mol/l) | log $K^0_{Mg2+}$ | log $K^0_{Ca2+}$ | log $K^0_{Zn2+}$ |
|---|---|---|---|
| 0.01 | 3.83 ± 0.05 | 4.29 ± 0.05 | 4.30 ± 0.05 |

For a given heparin concentration, the currents obtained in calcium or zinc chloride reference solutions in response to voltage pulses will be greater than the currents obtained in a magnesium reference solution. For a given insulin concentration, the currents generated will be greater in a zinc chloride solution than in calcium or magnesium chloride reference solutions.

The system and methods described herein are not limited to distinguishing small molecule analytes. As shown in Table 2, examples of analytes, by test type and reference solution for use with the system and methods of the invention are provided. Exemplary reference solutions comprise water soluble ionic salts, bio-molecules, antibodies, and immunoglobulins. Proteins have a characteristic pH at which positive and negative charges on the molecule balance out, rendering the protein electrically neutral. This pH is known as the isoelectric point (pI) of the protein. When the pH of an aqueous solution is adjusted to match the isoelectric point, proteins normally precipitate. For example, the pH of a 0.1 M solution of ammonium sulfate is 5.5. At this pH, insulin is electrically neutral. If a voltage pulse is applied, the resulting current will be exclusively the result of the conductivity of ammonium sulfate. By adjusting the pH of a reference solution, the identity of insulin (pI, 5.5), morphine (pI, 9.1), albumin (pI, 4.9) and γ-globulin (pI, 6.6) may be determined.

TABLE 2

| Analyte | Test type | Reference solution |
|---|---|---|
| KCl | Electro-chemical, thermal | Deionized water |
| Heparin | Electro-chemical | $CaCl_2$, $ZnCl_2$, $MgCl_2$ |
| Insulin | Electro-chemical, antibodies | $CaCl_2$, $ZnCl_2$, $MgCl_2$, immunoglobulins |
| Morphine | Electro-chemical | Ammonium sulfate |
| Albumin | Electro-chemical | Ammonium sulfate |
| γ-globulin | Electro-chemical | Ammonium sulfate |
| Propofol | Electro-chemical | Ammonium sulfate |

An advantage of the microfluidic cartridge 10 described herein is that only small reaction volumes are needed. The identity or concentration of an analyte can be determined by testing less than 1 mL of solution. By way of non-limiting example, the test sample can be less than about 1 mL, 500 µL, 250 µL, 100 µL, 50 µL, 25 µL, 10 µL, 5 µL, 2 µL, or 1 µL. Similarly, the volume of reference solution consumed in a test run can be less than about 1 mL, 500 µL, 250 µL, 100 µL, 50 µL, 25 µL, 10 µL, 5 µL, 2 µL, or 1 µL. Equal volumes of test sample and reference solution can be used or different volumes can be used, depending on the desired final concentration of ions during a given test. Accordingly, the final ion concentration in the test channel 40 during a test may be adjusted by selecting a reference solution at a specific concentration and/or by varying the proportions of test sample solution and reference solution. Accordingly, the solutions may be mixed in equal proportions or may be mixed in varying unequal proportions.

The test sample and the reference sample may be introduced into the test channel 40 as a stationary injection. Alternatively, the test sample and the reference sample may be introduced at a substantially constant flow rate. By way of non-limiting example, the test sample and reference solution may be injected at a flow rate between about 100 µL/s to about 1 µL/s, e.g., about 100 µL/s, 50 µL/s, 25 µL/s, 10 µL/s, 5 µL/s, 2 µL/s, or 1 µL/s. The test sample and the reference solution can be introduced at substantially the same rate or at different rates.

The microfluidic cartridge 10 can be made of any suitable material such as glass, polymer, e.g., polydimethylsiloxane (PDMS), plastic, e.g., whole-teflon, or combinations thereof. A difference between these materials is hydrophilicity. Polymers tend to be hydrophobic while glass and whole-teflon are hydrophilic. Hydrophobic surfaces, such as PDMS, tend to inhibit the passive capillary flow of aqueous solutions. Given that many test and reference solutions use water as a solvent, a pump may be required to maintain the flow of solutions through microfluidic channels made of hydrophobic materials. If capillary flow is preferred, the hydrophilic surface area of the channel walls can be increased to increase flow. To this end, glass and PDMS layers can be bonded together in a way that maximizes glass surface area of the inner surface of the microfluidic channels, while avoiding potential leaking along the edges of the channel. Alternatively, a whole-teflon cartridge may be used.

The reference solution channel 20, the sample channel 30, and the test channel 40 can be formed by etching, molding, milling, or casting, for example. The microfluidic cartridges 10 may be composed of multiple pieces that are attached, by forming the reference solution channel 20, the sample channel 30, and the test channel 40 in the surface of a first substrate and then attaching a second substrate over the channels to enclose them. The test channel 40 may have any suitable diameter and any suitable length, shape or configuration to allow mixing to occur. By way of non-limiting example, the diameter may be between about 1 mm to about 1 µm, for example, substantially about 1 mm, 500 µm, 250 µm, 100 µm, 50 µm, 10 µm, or 1 µm. By way of non-limiting example, the length may be between about 100 mm to about 1 mm, for example, substantially about 100 mm, 50 mm, 25 mm, 20 mm, 10 mm, 5 mm, or 1 mm. In various embodiments, the test channel 40 has a substantially round cross-section. However, rectangular or other cross-sections may be used. The sample channel 30 and reference solution channel 20 may have similar dimensions as the test channel 40. The sample channel 30 and the reference solution channel 20 are in fluid communication with the test channel 40.

The electrodes 50 may be made of any suitable conductive material, such as copper, silver, gold, platinum, palladium, and combinations thereof. In an embodiment, the electrode 50 is a platinum/palladium alloy. The electrodes 50 may be inserted before or after the test channel 40 is formed. In some embodiments, the electrodes 50 are positioned on opposing walls. At least a portion of the electrode tips projects into the test channel 40. The electrodes 50 are spaced apart to allow current to be tested across the fluid sample flowing through the test channel 40. The electrode tips may be spaced apart, for example, about 10 µm to about 1 mm. The electrodes may be substantially about 10 µm, 20 µm, 30 µm, 40 µm, 50 µm, 60 µm, 70 µm, 80 µm, 90 µm, 100 µm, 200 µm, 500 µm, or 1 mm apart. In some embodiments, electrodes 50 are placed at multiple locations along the length of the test channel 40. The current can be tested and measured in the reference solution channel 20, to calibrate for maximal current obtained by the reference solution alone, and to provide a within-experiment control.

Voltage is applied across the electrodes 50 and a response current is measured through the solution in the test channel 40. By way of non-limiting example, the voltage may be between about 1 mV to about 20 V, e.g., substantially about 1 mV, 10 mV, 50 mV, 100 mV, 200 mV, 500 mV, 1 V, 2 V, 5 V, 10 V, or 20 V. A voltage pulse can be transmitted to the electrodes 50 in pulses. By way of non-limiting example, the pulse may be between about 1 ms to about 1 s, substantially about 1 ms, 2 ms, 5 ms, 10 ms, 20 ms, 50 ms, 100 ms, 200 ms, 500 ms, or 1 s. Voltage pulses may be administered in rapid succession as a pulse train over a period of time in a single test run, for example, over a second or minute. Response current in the solution is measured by an amperage meter immediately after a voltage pulse, such as within about 10 ms of the pulse. A plurality of pulses may be administered to the same sample in a single test, and the current responses averaged to provide a more accurate reading. Voltage could be applied continuously. However, a pulsed approach makes it possible to apply voltage and measure the resulting current with the same pair of electrodes.

The microfluidic cartridge 10 may be single-use only or it can be reusable. In the case of a reusable microfluidic cartridge, the reference solution reservoir can be replaceable or refillable. The microfluidic cartridge 10 also may include a flush solution inlet for receiving flush solution to wash the test channel 40 between tests. Before reusing a given microfluidic cartridge 10, a washing procedure is implemented. The washing procedure includes after flushing one or more microfluidic channels, as needed, the corresponding reference solutions flow through the channels and their response profiles are assessed. If the measured responses do not match the expected responses for those reference solutions flowing in those channels, a new cartridge is used. Otherwise, the cartridge may continue to be used for additional testing.

Each microfluidic cartridge 10 can be pre-configured to detect specific analytes of interest, such as a compound or a class of compounds to be analyzed. In addition, the microfluidic cartridge 10 may contain a plurality of independent test channels, e.g., 2, 3, 4, 5, 6, 7, 8, 9, 10, or more, each with specific reference solution(s) and electrode(s), since each channel may have its own electrodes. Alternatively, a single reference solution reservoir may connect to multiple test channels. Microfluidic cartridges 10 can also be configured or reconfigured on-the-fly. The concentration of one or more reference solutions may be adjusted based on user input specifying the presumed analyte identity and concentration. The concentration adjustment is done online by adding the proper volume of solvent to the reference solution(s).

A plurality of microfluidic cartridges can be loaded into a single master device. The plurality of microfluidic cartridges may be similar or different, such that the master device is capable of measuring a variety analytes. Moreover, one or more cartridges may be used in a single analysis. For example, to detect multiple different analytes in a single test sample or to utilize multiple ions to detect a single analyte. Additionally, multiple channels can be etched into a single microfluidic cartridge, in series or parallel, to enable many tests to be performed per single use of a given cartridge.

Each drug analyte binds to particular ions with a specific affinity. In operation, a reference solution of ions known to interact with the analyte of interest is released from a prefilled reservoir through a reference solution channel 20 of the microfluidic cartridge 10. A small amount of test sample (e.g., <10 μL) suspected of containing the analyte is introduced or diverted into the microfluidic cartridge 10. The test sample enters the microfluidic cartridge 10 through a sample channel 30. The test sample and reference solution flow into a common test channel 40. The small size of the channel restricts turbulent mixing of the samples, leading to a precisely controlled diffusion gradient along the length of the test channel 40. While not being bound by any theory, it is believed that controlled diffusion along the length of the test channel 40 occurs due to the following: as the test and reference solutions travel side by side, the mix between solutions increases in a reliable and predictable manner as a function of distance along the test channel 40. Two variables determine the mixing gradient, including the point beyond which mixing is maximal: 1) the affinity between the solutions or the components in the solutions and 2) their initial concentrations. Consequently, measuring current-voltage relationships at several fixed positions along the channel aids in revealing both identity and concentration of the test solution. Identification is achieved by comparing currents from the point of expected maximal mixing, e.g., towards the far end of the test channel 40, in different test channels each with a different reference solution. Concentration is more comprehensively assessed by measuring the current gradient along different points of a given test channel and reference solution.

As the test sample and reference solution begin to mix, any analyte in the test sample will bind to the ions in the reference solution, changing the local concentration of free ions in the test channel 40. A short voltage pulse, e.g., amplitude between 1-5 V, duration between about 10-500 ms, applied across a pair of electrodes will generate a current that is proportional to the concentration of free ions at that location in the test channel 40. The generated current can be used as a proxy for the concentration of the analyte in the test sample.

For example, the presence and concentration of heparin in an intravenous solution, bag or syringe, i.e., the test solution, can be detected using a reference solution of aqueous $Ca^{2+}$ (e.g., CaCl at 5M). Heparin is known to bind and sequester $Ca^{2+}$. Thus, when a calcium solution is mixed with a small test sample from the intravenous bag, or a syringe filled with the solution, changes in the conductance profile of the mixture are dependent upon the concentration of heparin in the intravenous solution.

Individual measurements of currents in response to voltage pulses exhibit variability even if the amplitude of the voltage pulse and the concentrations of test and reference solutions are kept fixed. These measurements may be considered as the response, i.e. current, generated by a stimulus, i.e. voltage pulse amplitude and reference solution. For fixed stimulus and test solution concentration, a user may take several measurements at the point of maximal mixing between test and reference solutions to create a frequency histogram of observed responses. The histogram assigns an occurrence probability value to all responses whether they were observed, i.e., values between 0 and 1, or not, i.e., value of 0. By repeating this procedure at different test solution concentrations, a probabilistic response profile to a given reference solution is generated. The response profile indicates the likelihood the user will observe a response given a test solution concentration.

Using Bayes theorem, if the user knows the response profile ahead of time, the user may take a measurement and infer the test solution concentration most likely to have generated such response. In some instances, an estimation may be ambiguous. For example, if a test solution generates non-zero current responses in a narrow range of concentrations only. If a zero current response is obtained during measurement, the estimation assigns equal likelihood to a large range of test solution concentrations as the source of the observed response. In order to narrow the estimation of the concentration, a library of response profiles may be generated for different reference solutions ahead of time. Responses collected for each reference solution are considered to be statistically independent of one another. Consequently, individual concentration estimations can be combined in a multiplicative fashion to converge on a narrower concentration value range.

Probabilistic response profiles may be created to infer the identity of a test solution, independent of its concentration. As described herein, mixing of test and reference solutions in a microfluidic channel depend on the solutions' diffusion and binding coefficients. By measuring current responses along the length of the microfluidic channel at different test solution concentrations the user can measure the rate at which mixing occurs. The mixing rate may exhibit variability and be expressed probabilistically. In this case, the response profile indicates the likelihood the user will observe any mixing rate given a test solution identity. Similar to the concentration case, several test solutions could have similar mixing rates with a given reference solution. A way to distinguish the estimated identity of the test solution is to produce a library of mixing rate profile to several reference solutions. During measurements, individual identity estimations are combined to narrow the identity of the test solution.

In both cases, the combined probability across multiple reference solutions provides a quantitative value for the certainty of the estimation of the identity and concentration of the test solution.

Multiple tests with different reference solutions may be run in parallel or in series in order to ascertain the concentration and identity of an analyte of interest, such as a drug. Sets of tests may be designed to be mutually exclusive, so that if a battery of tests designed for drug X is used for drug Y, an error is raised. The microfluidic cartridges 10 may be used to implement such tests in order to detect drug identity or concentration by discriminating among a range of possible drugs and concentrations. The results compiled from one or more tests run on a given drug or analyte of interest provide the drug's electrochemical profile. Additional tests may be implemented using the system and methods described herein, in order to construct a comprehensive physical-chemical profile of the analyte, including electrochemical, chemical, biological, biochemical, physical, thermal or optical responses, comprising a signature that can uniquely identify the analyte and its concentration with a quantifiable degree of uncertainty or confidence. The response profile constructed from one or more tests may be compared against a library of known response profiles, in order to identify the analyte and/or the analyte's concentration. The matching of a response profile based on one or more tests to a known profile may be implemented by probabilistic, e.g., Bayesian, estimation methods. The responses of a given test sample to a set of tests may be matched to likely known response curves by a processor programmed to execute probabilistic analysis, with access to the library of known response profiles. Such analysis points to likely known response profiles, for an analyte of known identity and concentration, within quantifiable accuracy ranges. The faithfulness of determining drug identity or concentration based on the responses collected may depend on the range of drugs and concentrations available in the library. The library of response profiles may be developed and dynamically updated to include responses of various drug types and concentrations to various tests.

A similar approach may be used to detect combinations of two or more distinct analytes, e.g., drugs, at various concentrations mixed together in a single test solution. The tested responses of such a "compound" test solution, comprised of multiple drugs, differ in a measurable manner from the expected responses of any one of the individual drugs in the test solution analyzed in isolation. The library of expected responses to tests performed on a single drug may be developed to include expected responses to tests performed on that drug in the presence of other drugs that are potentially co-administered with the drug through a single route, e.g., the same IV line, or through multiple routes. The selection of performed tests takes into account such potential combinations of drugs. Similar to the discrimination of single-analyte test solutions, a processor unit is programmed to implement probabilistic estimation methods to identify the likely identity and concentration of the individual component analytes from a range of possible compound solutions composed of individual analytes at various concentrations.

Each battery of tests is implemented using a combination of one or more microfluidic cartridges 10, each containing one or more microfluidic channels, in any arrangement, configuration or shape. Each channel is loaded with one or more reference solutions and prepared for use with one or more detector units The detector units include, but are not limited to, electrode detectors, pH detectors, thermal detectors, optical detectors, antibodies, etc., each detector unit comprising a corresponding sensor, including but not limited to electrodes, pH sensors, thermal sensors, and photo sensors. For each drug to be covered by a given battery of tests, families of response curves for each reference solution and detector type are created. Each response curve is constructed by measuring one or more electrochemical, chemical, biological, biochemical, physical, thermal or optical properties of different mixtures of analyte and (ionic or other) reference solution, at different concentrations of the analyte and reference solutions. Such properties include, but are not limited to, the following examples: response current to a voltage pulse, temperature, pH reading, or light reflection. During real-time use, comparisons between the test outcomes and library data will provide the likely identity of the analyte and the analyte's concentration.

It is noted that the detection of analyte concentration is independent of the detection of the analyte's identity. The concentration of the analyte is detected based on the presumed identity of the analyte, which is provided by a user, RFID, smart infusion pump, or any other means.

It is also to noted that the detection of analyte concentration or identity is not restricted to intravenous or drug solutions. Any analyte in solution may be tested with the system, regardless of ultimate intended use of the solution, whether for a patient or any other use.

Figure 6:
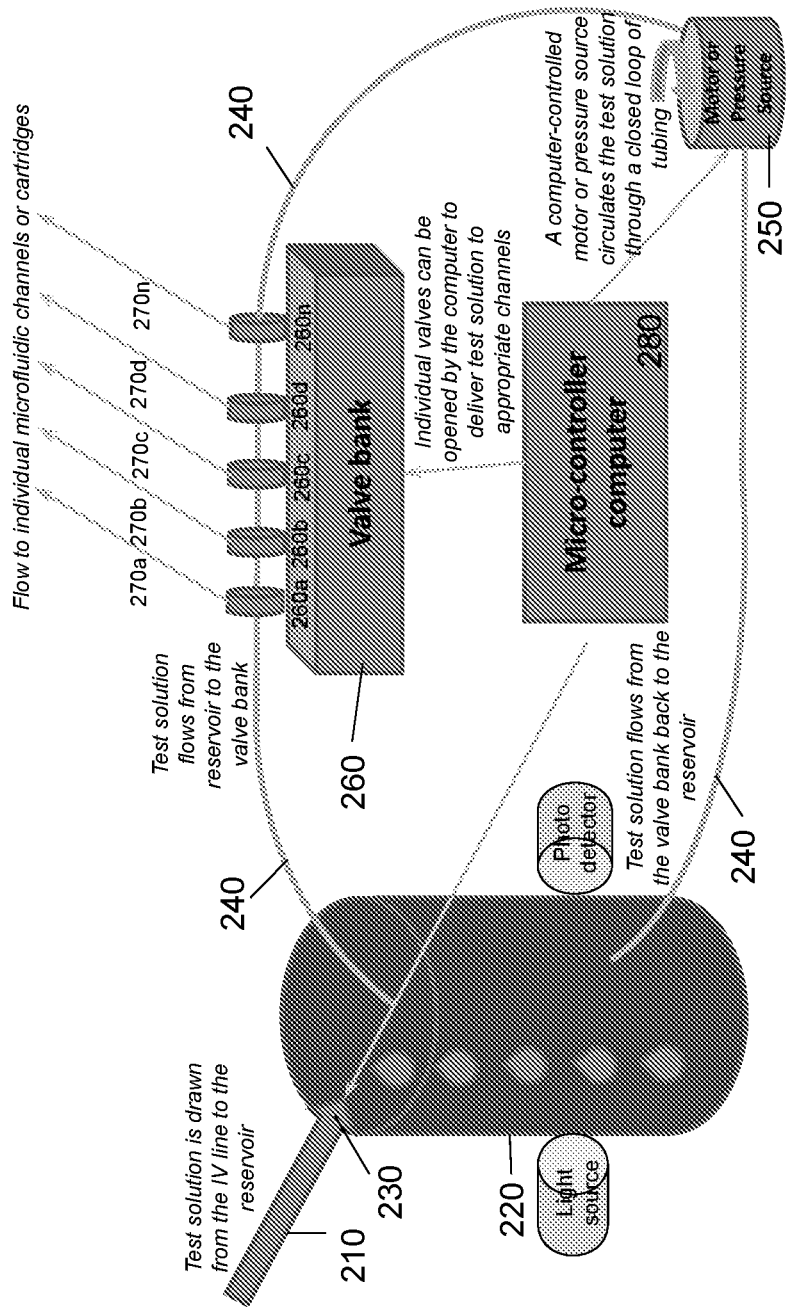
FIG. 6 is a schematic of an embodiment of a pump arrangement used to transport test and/or reference solutions of interest from their corresponding source into the microfluidic cartridge.

FIG. 6 shows a schematic of a pump configuration, in accordance with an exemplary embodiment. A first end of an external first tube 210 connects to an intravenous line (130 in FIG. 2) and a second end of the external tube flows into a test solution reservoir 220. Flow of the analyte of interest from the intravenous line into a test solution reservoir 220 is controlled by opening or closing a valve 230 that is connected to the external tube. The external tube 210 ends at the reservoir. The external tube 210 deposits a small, predetermined, volume of the solution flowing through the intravenous line upon opening of the valve 230. A set of photo detectors and corresponding photo sensors, and a light source (such as an LED of a particular wavelength) are arranged around the reservoir. At least one photo detector is placed directly opposite from the light source. Light is emitted continuously and the intensity of light arriving at the detectors is sampled at a high frequency. Transient deviations in the light intensity pattern allow for the measurement of the "drip" rate, which is directly related to the flow rate of the solution containing the analyte of interest. A separate second tube 240 is suspended inside or connected to the reservoir 220 and the second tube 240 travels serially through a set of valves 260 and through a rotating motor, e.g., a pump, 250 before looping back into the reservoir 220. Each of valves 260$a$-$n$ in the valve bank in turn is connected to a terminal tube 270$a$-$n$ that travels and is connected to the appropriate inlet, e.g., intravenous bag 32 in FIG. 1, of individual microfluidic cartridges 10. Valve 260$n$ indicates that any number of additional valves may be added. Rotation of the main motor 250 promotes flow of the solution from the reservoir 220 into the second tube 240. Individual valve openings of the valves 260$a$-$n$ at the valve bank determine which microfluidic cartridge 10 receives a sample of the test solution. The operation of the valve bank, including the valve connected to the main intravenous line 210, and motor 250 is controlled by a dedicated micro controller computer 280. The controller can set the speed of rotation of the motor 250 as well as the order and timing in which each of valves 260$a$-$n$ opens or closes. Similar sets of reservoirs, valve banks and motors are used to ensure the flow of predetermined reference solutions into the appropriate inlet of the corresponding microfluidic cartridges.

Given that interrogation of a sample test only requires a small volume of solution in a microfluidic cartridge 10, it is advantageous to minimize the length of the tubes carrying the test solution from the intravenous line 210 to the microfluidic cartridges 10. This holds the overall volume of solution drawn from the intravenous line 210 to a minimum. In this configuration, the system is preferably placed in close spatial proximity to the intravenous line 210. However, it is also possible to implement the system in additional locations, for example far removed from the intravenous line 210, with additional means of transferring required volumes of the test analyte to the system.

Patient Safety Systems

Microfluidic cartridges described herein may be integrated into patient safety systems designed to reduce or eliminate "never events." The patient safety system includes standard operating procedures designed to minimize errors and inconvenience.

Figure 2:
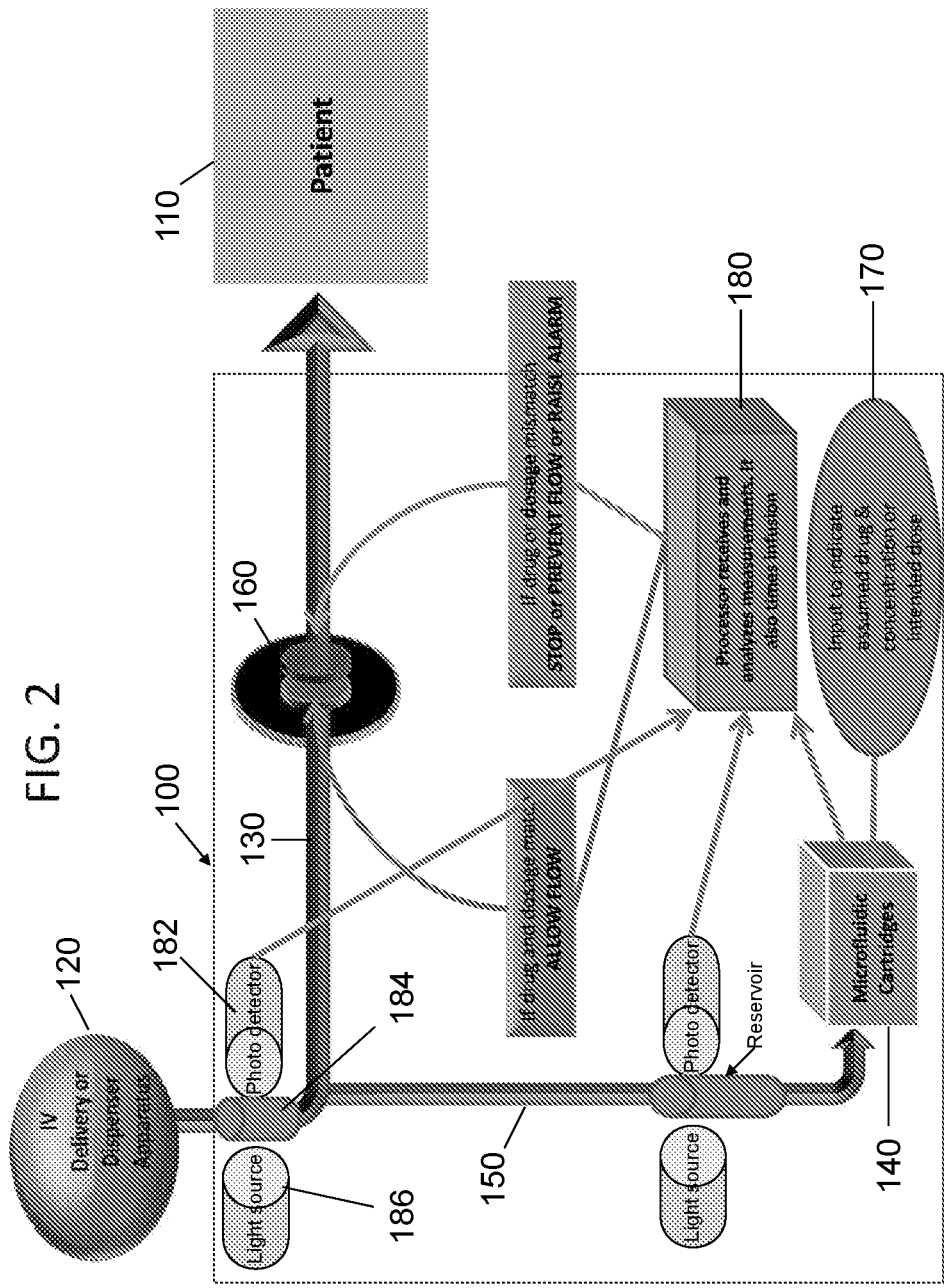
FIG. 2 is a schematic showing an embodiment of an infusion safety device system including the microfluidic cartridge.

FIG. 2 shows a patient safety system 100, in accordance with an exemplary embodiment. A patient 110 is connected to an intravenous dispenser apparatus 120 by intravenous line 130. The intravenous dispenser 120 comprises an intravenous bag, port, or other apparatus for delivery of intravenous drugs. The intravenous dispenser 120 may contain a drug or the port may accommodate infusion of a drug from a syringe or other injectable device. A microfluidic cartridge 140 is in fluid communication with the intravenous line 130. In one embodiment, a plurality of photo detectors 182, such as a photo sensor array, and a light source 186 (e.g., LED of a given wavelength) are arranged around a drip chamber 184 attached to the end of the tubing that connects to the intravenous dispenser 120. In another embodiment, the light source-photo detector assembly is placed around the reservoir that connects the intravenous line 130 to the microfluidic cartridge 140. In either case, at least one sensor is placed directly opposite from the light source 186. The light source 186 may emit light continuously. The photo detectors 182 sample the light intensity they collect with a predetermined sampling rate. The predetermined sampling rate may be a high, medium or low rate depending on the application. Because the walls of the drip chamber 184 or reservoir are made of translucent materials, typically plastic, the light beam will be diffracted and reflected as it travels through the walls of the drip chamber 184. The amount of light collected at each detector 182 is determined by the optical properties of the chamber wall. In the absence of any solution flow, the light intensity pattern across all detectors 182 is the baseline condition. As the solution flows through the chamber 184, discrete drops cross the light beam path and alter the overall diffraction/reflection of the light as it travels through the chamber 184. Counting the number of times the light intensity pattern is modified at the photo detector 182 in a pre-determined time window yields the flow rate in drops per unit time. This flow rate may be multiplied by a conversion factor, determined by the diameter of the intravenous tubing of the intravenous line 130 (units of volume per drop) to convert the flow rate into units of volume per unit time. In one embodiment, a test line 150 automatically diverts a portion of intravenous fluid from the intravenous line 130 to the microfluidic cartridge 140, which then tests the intravenous fluid to determine if the intravenous solution matches the prescribed solution. In some embodiments, the description of the prescribed solution, including assumed drug identity, concentration, dosage or dose, is provided as input 170 to the microfluidic cartridge 140, which acts as a patient safety device. The prescription can be pre-programmed into or transmitted to a processor 180 that controls the microfluidic cartridge 140 and a safety valve 160. The processor 180 comprises a clock or timer for monitoring the duration of an infusion. If a mismatch between tested and prescribed solution and dosage is detected—e.g., the intravenous solution contains the wrong drug and/or the wrong concentration of the right drug, and/or it is flowing at the wrong rate—the processor 180 closes the safety valve 160 in the intravenous line 130 to prevent patient infusion. An alarm, e.g., one or more of visible, audible, and tactile alert at the device or transmitted to a remote location, e.g., nursing station or quality control monitoring station, also can be triggered by the processor 180 if a mismatch is detected. Alternatively, if the identity of the tested and prescribed solutions match, but the intended concentration and/or flow rate is not as expected, the processor 180 keeps track of the elapsed time from the start of the infusion to enable the full prescribed dose to be administered. In an exemplary embodiment, an initial warning may announce the detected mismatch and the time the infusion should last to ensure the delivery of the prescribed dose. Once the full dose has been delivered, an alarm may be triggered by the processor 180 to stop the infusion. In some cases, the processor 180 may adjust the flow rate to deliver the desired dose over the desired infusion period. Such adjustment can occur via communication by the processor 180 with the infusion pump or mechanical clamp on the infusion line.

Figure 3:
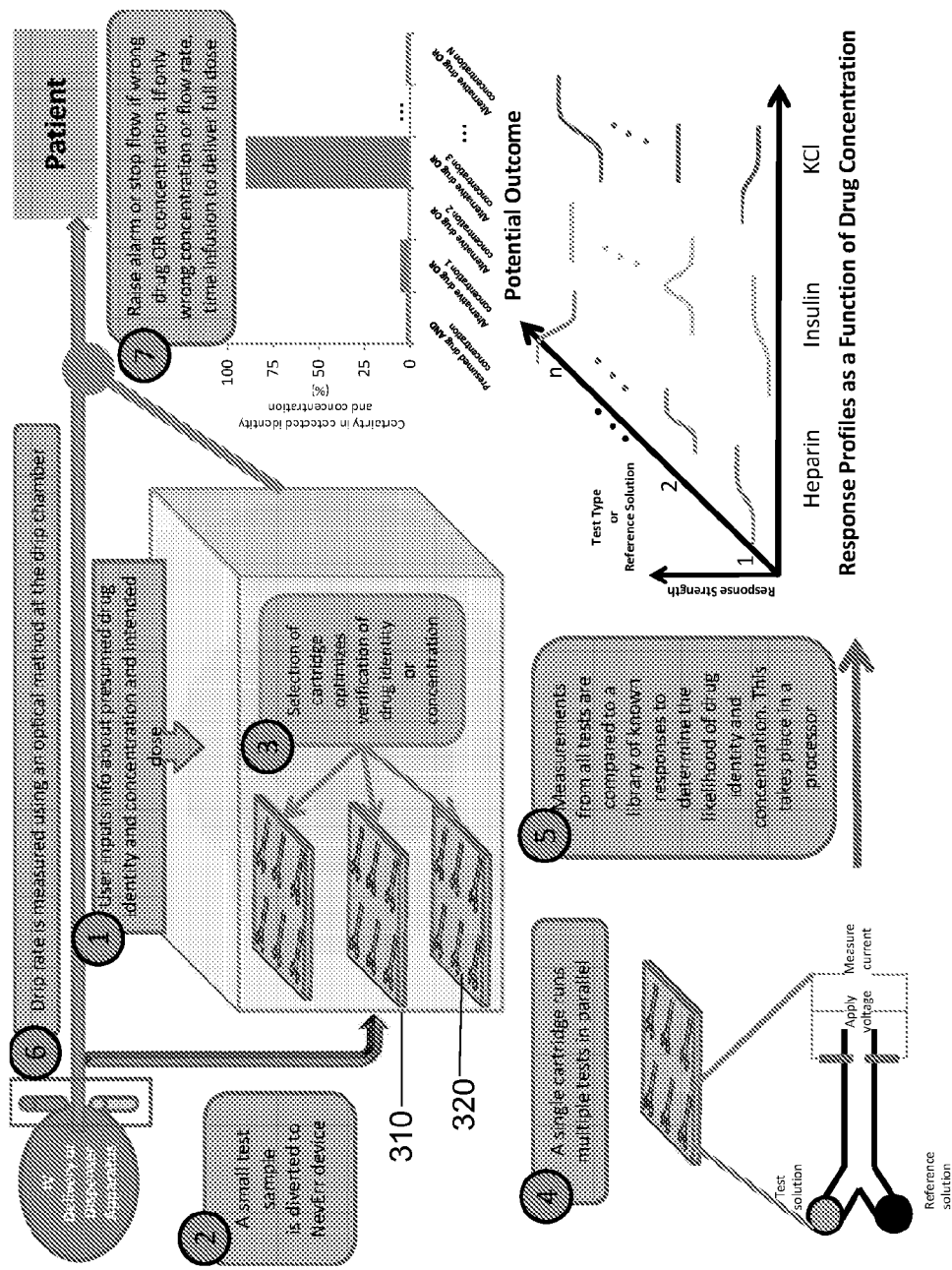
FIG. 3 is a schematic showing an embodiment of an infusion safety device system including a graph of response profiles as a function of drug concentration.

FIG. 3 is a schematic showing an embodiment of an infusion safety device system including a graph of response profiles as a function of drug concentration. In particular, FIG. 3 shows an example of the system 100 when used to confirm one or more of the identity, concentration, dosage, and dose of a drug in a test solution. In step 1, a user inputs information about one or more of the identity, concentration, dosage, and dose of the intended, e.g., prescribed, drug. This information may also be transmitted automatically to the device, e.g., via RFID, barcode reading, or wireless communication, without the user explicitly or manually providing input) into a microfluidic device 310. In step 2, a test sample is diverted to the device 310. In step 3, a microfluidic cartridge 320, i.e., cartridge containing one or more microfluidic channels described herein, is selected from a bank of available cartridges. The selection of the cartridge 320 may depend on the presumed drug identity, concentration, dosage, and dose, and is made in a way that optimizes the performance of the device 310. In some cases, a combination of cartridges may be selected and used in series or parallel. In step 4, one or more tests are performed on the test sample with the selected cartridge 320, in order to confirm one or more of the presumed drug identity, concentration, dosage, and dose. In step 5, measurements obtained from these tests are compared to known reference data to determine one or more of the identity, concentration, dosage, and dose of the drug in the test sample. The comparison takes place in a processor, such as the processor 180 described above with respect to FIG. 2, housed in the device 310 but separate from the microfluidic cartridges 320. In step 6, the drip rate is measured using a light emitter-receptor assembly around the drip chamber. In step 7, an alarm is raised if a mismatch is detected between the identity of the tested drug and that of the presumed drug. An alarm may also be raised if there is a mismatch between the concentration of the tested drug and that of the presumed drug. An alarm may also be raised if there is a mismatch between the dosage of the tested drug and that of the presumed drug. The tested drug's dosage is estimated based on the tested concentration and the measured flow (or "drip") rate. If the identity and dosage of the tested drug match those of the presumed drug, the drug is administered to the patient. In some cases, the total dose, i.e., volume of drug administered, is of concern, not only the dosage, i.e., dose administered per unit time. To address this, the device 310 tracks the time elapsed from the start of the infusion, and based on the estimated flow rate and detected concentration of the drug, the device calculates the duration of infusion needed to deliver the total dose. The device 310 times the infusion and raises an alarm or alerts the medical staff at the end of the desired infusion period, in order to ensure that the intended dose has been delivered. The device 310 may also adjust or stop the flow of the infusion at any point during the desired infusion period, or at the end of the desired infusion period. The graph in FIG. 3 entitled "Response Profiles as a Function of Drug Concentration" illustrates a response profile for a subset of drugs (Heparin, Insulin and KCl) at several concentrations to "n" different reference solutions. By comparing the measurements obtained in step 4 to the response profiles corresponding to the presumed drug (column), the most likely concentration to have generated the observed response is determined. Similar response profiles may be generated that quantify the rate of mixing for different drug and reference solution combinations. By performing a similar comparison, the most likely drug responsible for the observed rate of mixing is identified. These comparisons may be stated in probabilistic terms. Thus, the presumed drug identity and concentration, along with alternative drugs and/or concentrations, are assigned a specific likelihood. The values of these probabilities range between 0 and 1 and indicate the certainty with which one or more of the drug identity, concentration, dosage, and dose are estimated. The outcome of comparing the measurement from step 4 to the library of profiles is illustrated in the graph in FIG. 3 entitled "Potential Outcome."

In some embodiments, the microfluidic cartridge 140 is installed in-series, i.e., in-line, with the intravenous line 130 and in some embodiments the microfluidic cartridge 140 is installed in parallel, i.e., branched, with the intravenous line, 130. In some embodiments, multiple microfluidic cartridges may be installed in a single device that can receive fluid input (test samples) from multiple sources, e.g., multiple IV lines.

In exemplary embodiments, the system 100 includes the following components: input device, micro controller, acquisition unit, micro pump system, mechanical units, clock, processor, light emitter—photo receptor assemblies, microfluidic cartridges, and output devices. The input device, which may include a touchscreen, keypad, USB, Ethernet or wireless port, or any other means for inputting data, is used by a user to specify the assumed/expected drug identity and concentration as well as the desired dose (mg) and intended dosage (e.g. mg/min or mg/hour). The input of information can be done manually, by interacting with the keypad or touchscreen, or automatically, by having a bar scanner (e.g., RFID) or a central computer communicate directly with the system via USB, Ethernet or wireless ports. The input device may be connected to a micro controller which, in turn, is connected with a micro pump system, a signal acquisition system (A/D converter, amplifiers and clock), output devices (display, audio, electro-mechanical clamp or valve, and USB, Ethernet or wireless connectivity ports) and mechanical units (loading unit used to replenish microfluidic cartridges as needed, clamps used to hold and dispose of cartridges). Upon entry of information about desired dose and intended dosage, the processor records the light intensity collected at each photo receptor in the absence of liquid flow to establish a baseline light intensity pattern. Next, the photo receptor continues to sample the light intensity at a predetermined rate and records the times at which the pattern across all photo receptors changes because of the temporary alteration in overall diffraction/reflection introduced when a drop of liquid crosses the path of the light beam inside the drip chamber. Once a predetermined time interval has passed, the processor calculates the drip rate as the number of times the collective light intensity pattern deviated from baseline in said interval. The flow rate is calculated by a conversion factor determined by the diameter of the intravenous tubing. Upon entry of information about expected drug identity and concentration, the central controller directs the pump system to draw a sample from the intravenous line into a predetermined set of microfluidic cartridges. The microfluidic cartridges may be pre-loaded ahead of the test, or loaded at the time of the test. The number and order in which these cartridges are used for a given analyte are selected by the controller, depending on the user information provided as well as the outcome of the initial tests. Once flow has been established, the control unit drives the delivery of voltage pulses and the recording of the resulting ionic currents. Next, a program executes to determine measures of central tendency (mean, standard deviation, etc.) of the recorded data from each of the microfluidic cartridges. If measurements match the expected behavior given the expected identity and concentration of the test solution, the micro controller may: 1) issue a message that confirms the identity and concentration and 2) open the valve that allows flow of the intravenous line into the patient's arm. If the measurements do not match the expected behavior of the test solution, the micro controller may: 1) direct flow of the test solution into additional microfluidic cartridges for further testing; 2) raise an alarm displaying the error indicating wrong medication or incorrect concentration, log the error, test results and associated information to a storage device, e.g., hard-drive, and/or communicate the error to a centralized/networked computer via Ethernet, wireless, USB or other network connection; 3) close the valve that prevents the flow from the intravenous line into the patient's arm; or 4) if the mismatch occurs only between the assumed drug concentration or expected flow rate to meet the intended dosage, the processor allows the infusion to proceed, start a timer, issue a warning about the encountered mismatch and the time it would take to deliver the desired dose and raise an alarm once the full dose has been completed. Once testing has finished, irrespective of result, the processor may: 1) direct the clamp holding the recently used cartridges to release them into a trash bin, 2) count the number of remaining cartridges for future tests, 3) assess the space left in the trash bin and 4) display appropriate information informing the user to take appropriate actions, e.g., empty bin, replenish cartridges, service unit, etc.

In some embodiments, the microfluidic cartridge 140 tests the intravenous solution in real-time, and the safety valve 160 is closed only if there is a mismatch. In some embodiments, the safety valve 160 is closed by default and/or an infusion pump is stopped until microfluidic analysis is performed and the identity/concentration of the intravenous solution confirmed. Upon confirmation, the safety valve 160 is opened automatically or manually, and/or the infusion pump is activated, thereby permitting patient infusion.

The patient safety system 100 may be situated at different locations, depending on the desired application. For example, the system 100 can be located at the bedside just before the point of entry to the patient, functioning as a gatekeeper between one or more intravenous bags or injection ports 120 in the IV line(s) 130 and the patient. Alternatively, the patient safety system 100 can be centrally located at the site of drug preparation, e.g., hospital pharmacy or manufacturing plant, to confirm that intravenous bags, prefilled syringes and other containers of injectable solution are filled with the proper contents (drug type and concentration), meet appropriate levels of quality, or are properly labeled.

The microfluidic cartridge 140 may be in communication with and/or controlled by a control interface, such as a computer. The control interface may transmit instructions to the microfluidic cartridge 140, such as to open valves and operate pumps to move fluid through the microfluidic cartridge 140. The control interface also may receive data from the microfluidic cartridge 140, such as amperage measured in the test channel. The control interface can include software that when executed, calculates the conductance across the test channel and extrapolates the identity and/or concentration of the analyte in the test sample. The control interface also can control the safety valve in the intravenous line 130 to start or stop patient infusion. The control interface may display the conductance profile on a graphical user interface, such as a monitor, or the control interface may trigger an alarm (e.g., visible, audible, and/or tactile) that a mismatch has been detected.

The patient safety system 100 minimizes errors in intravenous drug identity or dosage (concentration and/or flow rate). Drug identity and concentration are confirmed en route to the patient, and preferably the analysis is performed as close as possible to the point of entry to the patient 110. In bedside embodiments, the patient safety system 100 may include a safety valve that prevents intravenous solution from flowing to the patient. The system 100 is straightforward and easy to use. For example, a healthcare professional prepares an intravenous bag and attaches it to the patient safety system 100. A small sample of the intravenous solution is diverted to a microfluidic cartridge 140 that verifies the identity and concentration of an analyte of interest (e.g., a drug) in the intravenous solution. The patient safety system 100 may be programmed in a variety of ways to analyze the intravenous solution: for example: (i) the patient safety system 100 may be pre-programmed to expect a particular intravenous solution to be delivered to the patient; (ii) the prescribed intravenous solution may be transmitted automatically from the pharmacy to the patient safety system at the bedside; or (ii) the prescribed intravenous solution may be manually entered by a healthcare worker. Once the identity and dosage (concentration and/or flow rate) of the drug test correctly the safety valve is opened.

The microfluidic cartridge 140 of the patient safety system 100 analyzes the concentration and/or identity of an infusible compound—e.g., a pharmacological therapeutic agent, a diagnostic agent (radio tracer for imaging)—and the patient safety system 100 gates the infusion flow to the patient, pending correct drug identity and concentration.

In some embodiments, the intravenous solution is assessed at the initiation of infusion and before any intravenous solution enters the patient 110. The 160 valve may be controlled by the control interface of the patient safety system 100 is initially closed, preventing patient infusion. Among other options, the valve 160 can take the form of a clamp placed around the intravenous line 130 en route to the patient that can be tightened or released (like a cuff) by an electrical signal from the interface controller. The intravenous line 130 is filled with the intravenous solution to be infused and a small drop is siphoned into an input port of the microfluidic cartridge 140 for analysis. The intravenous line 130 is attached to the patient's intravenous entry port as the valve 160 remains closed, preventing flow to the patient 110. The presumed identity and concentration of the compound are used as inputs to the microfluidic cartridge 140 (either manually entered, scanned or digitally transmitted). Based on the inputs and other settings, the microfluidic cartridge 140 performs one or more tests on the sample drawn from the line 130. Based on the results of the testing performed, the microfluidic cartridge 140 can either open the valve 160 and allow flow to the patient 110 controlled by the infusion pump, raise an alarm and continue to prevent flow, or communicate with external equipment or systems, e.g., infusion pump or controller computer, to prevent, stop or adjust rate of flow in the intravenous line 130 to the patient 110. Such communication can be mediated by an external computer connected directly to the device or via a network link. Alternatively, the microfluidic cartridge 140 may communicate directly with a suitable infusion pump via USB, Ethernet, optical or other communication mechanism, in order to control the flow of the injectable/infusible solution to the patient 110.

In some embodiments, intravenous fluid is monitored after infusion has begun. For example, the intravenous fluid can be monitored continuously or at periodic intervals during infusion. A small test sample is siphoned from the intravenous line 130, with or without closing the safety valve 160. One or more tests can be run on the sample while infusion continues. If a mismatch is detected, an alarm is raised and the safety valve 160 is shut.

The detected identity or concentration of the test solution, e.g., drug, can be cross-referenced with the known characteristics of the patient, e.g., allergies, symptoms, biomarkers, monitored signs, and chart (written, electronic or otherwise)

or doctor's orders, and the administration of the drug can be prevented, stopped or adjusted by the microfluidic cartridge 140, if there is a mismatch between any of these and the detected drug or concentration. Such cross-referencing can be achieved by interfacing with a networked computer or accessing a database containing relevant patient data, hospital protocols and doctor's orders. The processor unit in the microfluidic cartridge 140 may compare the detected identity and concentration of the test solution with a stored or networked look-up table of allowable drugs and dosages, calculated from the concentration and rate of flow, if relevant. The rate of flow can be detected via a simple sensor in the microfluidic cartridge 140 in fluid communication with the IV line 130, or via input to the microfluidic cartridge 140 by the user or from an interface with a suitable infusion pump. If a potential mismatch is found between the detected and allowable drug and dosage value, the microfluidic cartridge 140 can raise an alarm or prevent, stop or otherwise adjust the flow of the drug to the patient 110.

A similar approach can be used to detect potentially unsafe mixtures of two or more drugs. Based on the microfluidic cartridge's 140 ability to detect and analyze compound test solutions, comprised of multiple drugs, the microfluidic cartridge 140 can detect potentially unsafe drug-drug interactions. These can be cross-referenced with the patient's characteristics and (written, electronic or otherwise) chart or doctor's orders, in order to prevent administration of potentially unsafe drugs to the patient.

Figure 7:
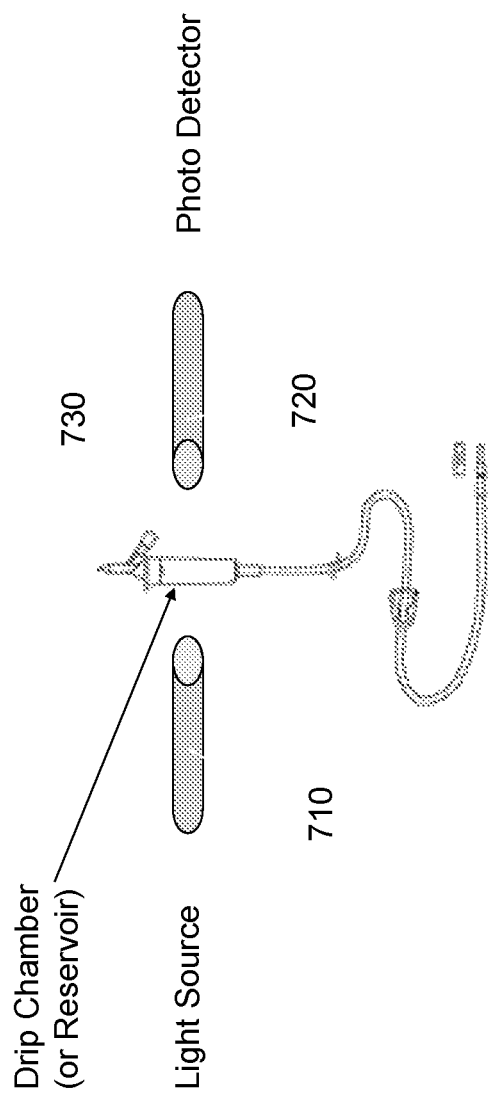
FIG. 7 is a schematic of an embodiment of an optical detector system for detecting and measuring the flow rate of a test solution.

FIG. 7 is a schematic of an embodiment of an optical detector system for detecting and measuring the flow rate of a test solution. An optical detector system comprises a light source 710 and a plurality of photo detectors 720 arranged around a drip chamber 730. At least one photo detector 720 is placed directly opposite from the light source 710. The drip chamber 730 is coupled to an IV line. The light source-detector assembly is in direct communication with a processor that controls the measurement schedule. The light source emits light 710 continuously. The photo detectors 720 may sample the light intensity they collect with a high sampling rate. Because the walls of the drip chamber or reservoir are made of translucent materials, usually plastic, the light beam will be diffracted and reflected as it travels through the drip chamber. The amount of light collected at each photo detector 720 is determined by the optical properties of the chamber wall. In the absence of any solution flow, the light intensity pattern across all detectors is the baseline condition. As the solution flows through the chamber 730, discrete drops cross the light beam path and alter the overall diffraction/reflection of the light as it travels through the chamber 730. Counting the number of times the light intensity pattern is modified at the photo 720 in a predetermined time window yields the flow rate in drops per unit time. This flow rate may be multiplied by a conversion factor, determined by the diameter of the intravenous tubing (units of volume per drop) to convert it into units of volume per unit time. The measured flow rate is stored by the processor.

Figure 8:
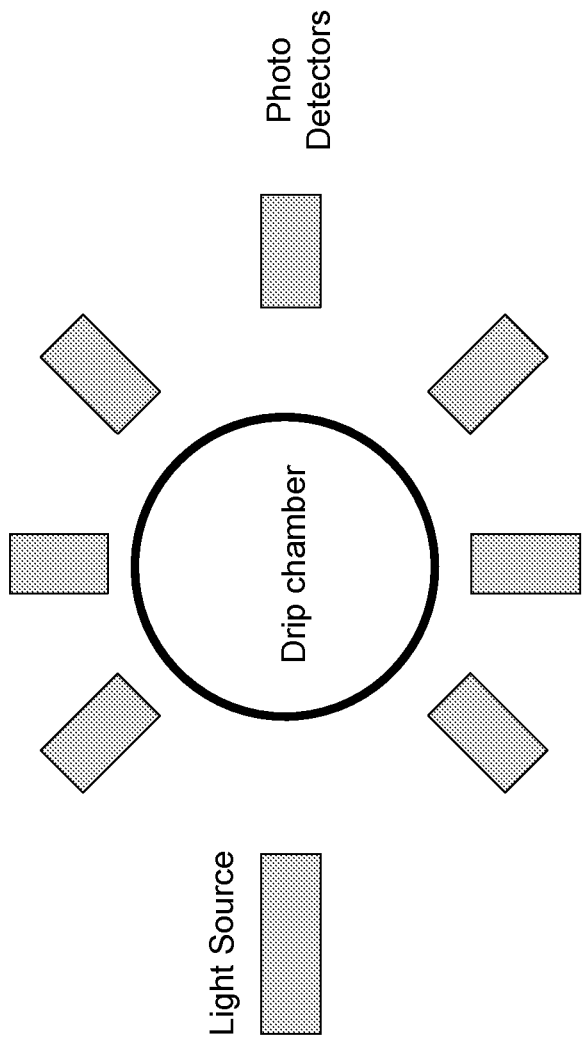
FIG. 8 is a cross-sectional view of an embodiment of an optical system for detecting and measuring the flow rate of a test solution.

FIG. 8 is a cross-sectional view of an embodiment of an optical system for detecting and measuring the flow rate of a test solution. In particular, FIG. 8 depicts the optical system comprising a plurality of detector arrays and emphasizes the need for several photo detectors to prevent random light intensity fluctuations in any given sensor to be counted (incorrectly) as a fluid drop crossing the light path.

Additional Types of Tests Implementable with the System and Methods of the Invention In some embodiments, silver nitrate may be used to measure the concentration of potassium chloride. For example, pairs of electrodes are placed along the length of the test channel 40 at predetermined intervals, for example at equidistant intervals. A reference solution of silver nitrate is introduced into the test channel 40 with a test sample containing potassium chloride. Potassium chloride and silver nitrate mix through diffusion, producing a silver precipitate deposited at the bottom of the test channel 40. As the two fluids travel down the test channel 40, a mixing area arises from the center of the test channel 40 out towards the edges of the test channel 40. For a given solution concentration, this mixing area widens as a function of the length of the test channel 40. The mixing area is narrowest at the point where the fluids first come in contact with one another, upstream of the test channel 40, and widest towards the end of the test channel 40, displaying a cone-like shape. At any given point along the length of the test channel 40, the width of the mixing area is proportional to the concentration of the silver nitrate and potassium chloride solutions. Hence, the width of the deposited silver "wire" is proportional to the concentration of potassium chloride. Larger concentrations of potassium chloride generate a wider silver wire earlier in the test channel 40. Hence, the concentration of potassium chloride can be assessed by identifying the position along the length of the test channel 40 at which the first pair of electrodes 50 becomes connected by the silver wire. The connectivity of any given pair of electrodes 50 may be measured by assessing conductivity with small voltage pulses.

In some embodiments, antibody binding tests may also be implemented to detect and measure analytes that bind immunogolublins, e.g., insulin. Antibodies can be added to an ionic solution with known composition and conductivity. When flowing through the microfluidic test channel 40, the antibodies bind to the analyte in the test sample, e.g., insulin, in proportion to the concentration of the analyte. Due to its greater size, each bound antibody-analyte complex displaces a larger number of ions than an unbound antibody. At any given position along the test channel 40, the bound antibodies displace electrolytes in proportion to the concentration of the analyte, resulting in a predictable and detectable change in conductivity.

In some embodiments, thermal tests can be added to the microfluidic cartridge 10 to further enhance analyte recognition and quantification. For example, given that potassium chloride is an ionic solution, applying a voltage pulse in the absence of a reference solution will produce a current that is proportional to its concentration. The same is true for a calcium chloride solution. One way to discriminate between these two ionic solutions would be to use water as a reference solution in a microfluidic channel. Mixing potassium chloride with water is an endothermic reaction, i.e., it absorbs heat from the environment, whereas mixing calcium chloride with water is an exothermic reaction, i.e., it releases heat to the environment. The change in temperature produced by the reaction can be detected by embedding a set of thermocouples along the length of the microfluidic test channel 40. While in this case the ionic currents in response to voltage pulses could be ambiguous in determining the identity of the test solution, measuring the change in temperature in response to mixing the solution with water would aid in enhancing the identification of the ionic species.

Potassium chloride would result in a drop in temperature, while calcium chloride would produce an increase in temperature.

In some embodiments, optical tests could be used to enhance analyte identification and quantification. The microfluidic cartridges 40 may be used in conjunction with a laser and photo detectors to detect optical properties of the test and reference solutions and of their mixture. For example, test solutions comprised of insulin or heparin, which both tend to bind to zinc ions, can be discriminated optically. Mixing either test sample with zinc chloride produce a drop in free zinc ions and the corresponding ionic current in response to a voltage pulse. However, heparin and insulin display different aggregation patterns once they have bound with zinc ions. Consequently, the new ion-analyte complexes, e.g., heparin-zinc or insulin-zinc, display different optical properties, such as light absorption and reflection. To determine the identity of the test solution, a laser pulse or other light source, e.g., diode of narrow or broad band, may be directed toward the mixed test-reference solution, with the resulting amount of light being reflected measured by one or more photo detectors.

In addition to being used to detect errors in drug identity or concentration, the microfluidic cartridges 40 may incorporated into a patient safety device that stores a time-stamped log of all drugs, including type and concentration, that have been administered to a given patient. Such information can be used upon deterioration of the patient's condition to identify potential causes, or offline to study aspects of treatment and disease management, including, but not limited to, understanding the effect of variations in concentration on treatment outcomes. The log can be written to an external computer or directly to a local storage device (e.g., hard drive).

In some embodiments, a patient safety system based on the microfluidic cartridges 40 described herein detect, and then indicate, alert against, stop, or prevent, the occurrence of potentially unsafe drug administration, including, but not limited to, potentially unsafe drug-drug interactions or the administration of drugs contrary to hospital or other relevant treatment guidelines or protocols. Such a system can analyze the drugs prior to administration to the patient, using the methods and microfluidic cartridges described herein, or other methods or mechanisms. The system can monitor and track the history of all drugs administered to the patient within a relevant time period, and compare drugs that are about to be administered to the patient against the patient's known characteristics, including allergies, condition and disease, as well as the doctor's orders, and hospital policies. If this comparison signals a potentially unsafe event, with a likelihood exceeding a predefined tolerable threshold, the system can alert the user or send a warning message to another site, e.g., nursing station, hospital-based network server, or healthcare practitioner or provider. Even in the absence of potentially unsafe events, the system can store and send messages to any of these locations or individuals, in order to provide periodic notification of drug administration.

Patient safety systems are but one possible application of the invention. The microfluidic cartridge 40 is versatile and the devices, systems and methods disclosed herein for patient safety readily can be adapted to any situation where detection of analytes and/or their concentrations are desirable. Such applications may or may not include alarming, automatic shutoff of fluid flow, and automatic disposal of product, as appropriate. For example, microfluidic cartridges can be used by quality control departments, e.g., in pharmaceutical companies or distributors, to verify chemical reagents or drugs prior to packaging, prior to shipment, or prior to stocking Microfluidic systems may be configured as portable devices for field use. In the case of solid analytes, the analyte could be dissolved or suspended in a suitable liquid for testing in a microfluidic channel.

Aside from patient safety devices, in some embodiments, the microfluidic cartridges can be used for quality control purposes, e.g., at pharmacies or manufacturing plants. Diminished efficacy of drugs can be due to their inability to bind to vehicles, most likely blood proteins, or to affect target sites. For example, in the case of antibiotics such as cephalosporins, reference solutions containing either blood proteins such as plasma protein fraction or peptidoglycan polymers would reveal the drugs' ability to bind to its transport or target agent, respectively. Using reference solutions with known binding affinities to an active ingredient, the microfluidic cartridges can be used to determine the efficacy as well as the concentration of an analyte within desired ranges. Quality control measures entail a broader set of reference solutions to be used, potentially requiring more controlled environments, e.g., temperature, lighting, etc., than by the patient's bedside. These additional constraints may be applied to the microfluidic cartridges incorporated into quality control devices.

The following examples are provided for illustration, not limitation.

Example 1

In one embodiment, a heparin containing solution was distinguished from a control solution using a microfluidic cartridge. In this embodiment a microfluidic cartridge was fabricated by irreversibly bonding a layer of polydimethylsiloxane (PDMS) to a glass slide. Prior to bonding, a Y-shaped microchannel (100 μm diameter, 20 mm length) was molded in the PDMS layer. A pair of planar Pt/Pd electrodes was deposited on the surface of the glass slide with a gap of 90 μm between the electrodes. The PDMS and glass layers were aligned so that both electrode tips remained within the channel.

A calcium chloride solution was prepared by mixing 7.45 g of calcium chloride dehydrate in 10 mL of water to obtain a 5M concentration. The sample solution included either: (1) injectable saline (0.5 mL, 0.9% sodium chloride Injection, USP) or (2) heparin (500 IU) mixed in injectable saline (0.5 mL, 0.9% sodium chloride Injection, USP), i.e., roughly 100 times the concentration that would typically be used for a patient weighing 100 lbs.

Controlled laboratory tests were performed to discriminate between the two different sample solutions. Heparin is known to bind $Ca^{2+}$, thus a 5M calcium chloride solution was used as the reference solution. In separate experiments, one or the other test solution was introduced into the microfluidic cartridge through its respective channel at a uniform flow rate of 0.10 μL/min, using a pump. At the same time, the reference (saline) solution was pumped into the microfluidic cartridge at a similar constant rate. As soon as both the reference and test solutions were flowing in the test channel, a train of 100 voltage pulses (2 volts) was applied via the electrodes. The resulting current was measured 10 ms following each voltage pulse. The test lasted less than 2 minutes.

More specifically, a 10 μL Hamilton syringe was loaded with either test solution or reference solution. The syringes were connected to a single syringe pump (Kent Scientific Genie Plus), whose flow rate was set to 0.10 μL/min.

Polyamide Capillary columns (Fisher Scientific) communicated each syringe with the appropriate inlet of the microfluidic cartridge. Flow was initiated simultaneously on both of the test and reference channels. Once flow was established, voltage pulses were delivered using a Keithley picoammeter/voltage source (Model 6487) through the output of the voltage source and currents measured through its input. Data were analyzed using Microsoft Excel software by comparing the mean current response of each condition.

Figure 4:
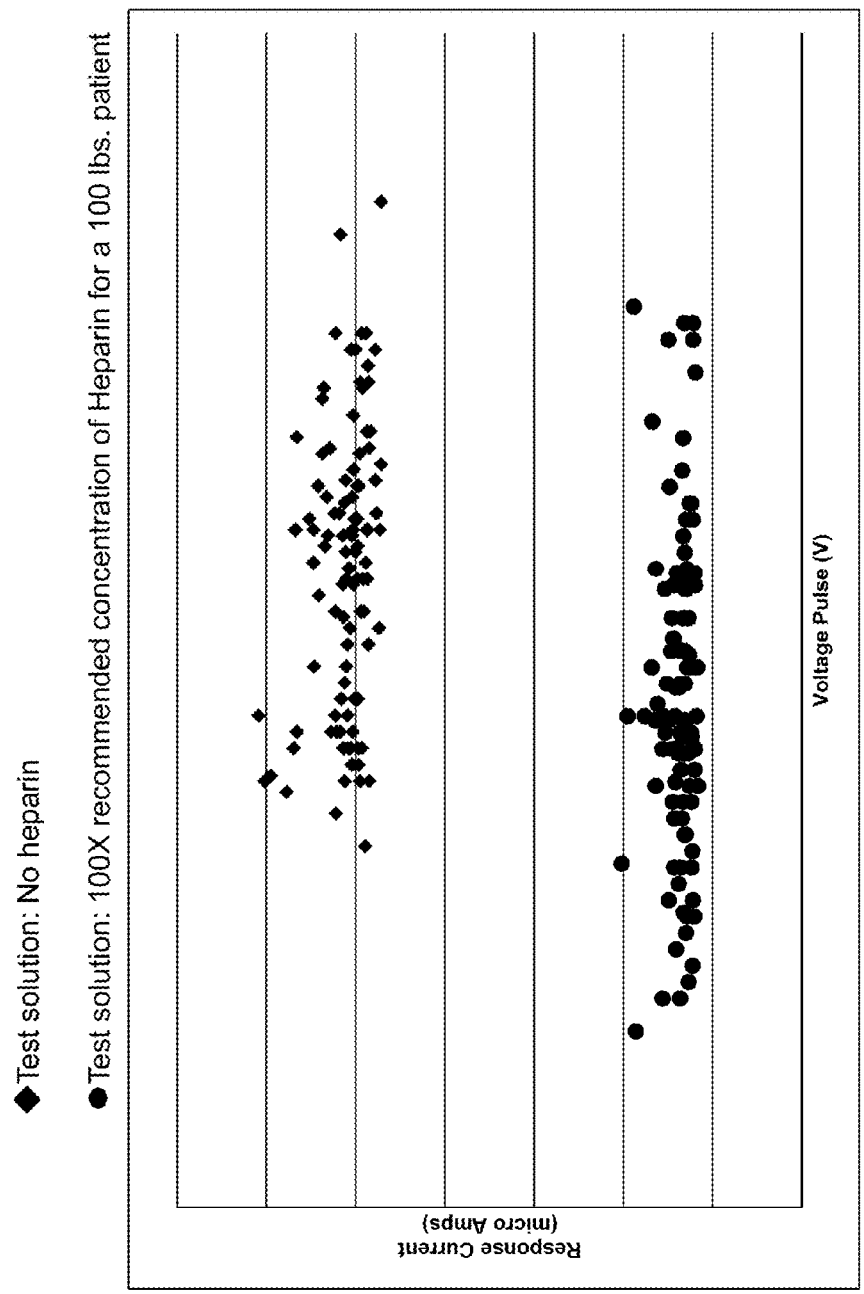
FIG. 4 is a graph showing an example of the detection of heparin using a microfluidic cartridge.

Referring to FIG. 4, the heparin test sample produced an average current of 0.14+/−−0.01 mA, while the saline solution produced a significantly (Student's t-test ($p<0.01$)) higher average current of 0.5+/−0.02 mA. As demonstrated by FIG. 3, a heparin saline solution can be distinguished from a saline solution using a $Ca^{2+}$ reference sample because each solution generates a significantly different current in the microfluidic cartridge.

Example 2

Different concentrations of heparin can be discriminated using the microfluidic cartridge and controlled laboratory tests of Example 1.

Figure 5:
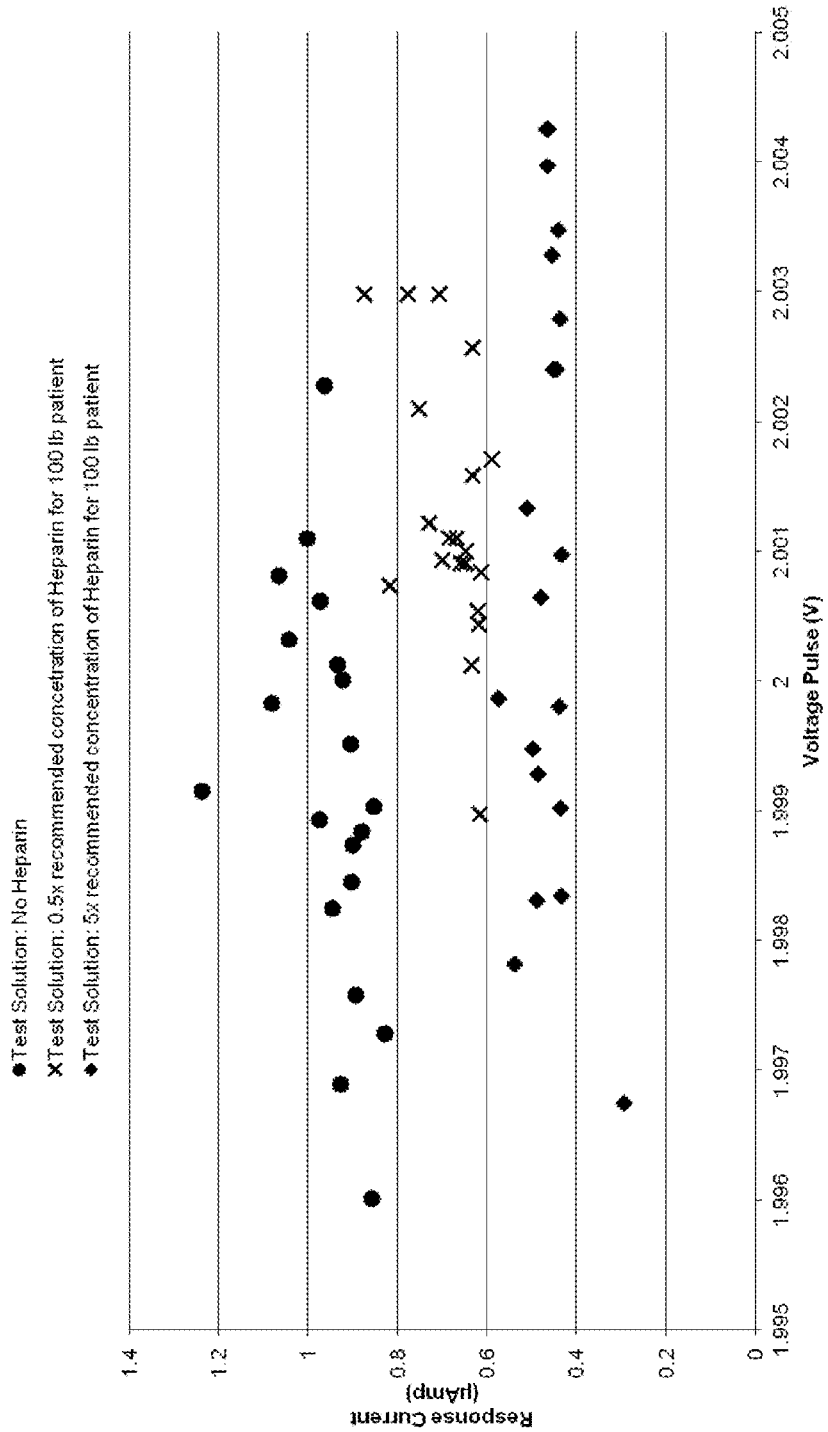
FIG. 5 is a graph showing an example of the detection of different heparin concentrations using a microfluidic cartridge.

Referring to FIG. 5, three different test solutions were prepared: (1) heparin diluted in injectable saline at half the typical dose for a 100 lb patient; (2) heparin in saline at five times the typical dose for a 100 lb patient; or (3) injectable saline (0.5 mL, 0.9% sodium chloride Injection, USP). The reference solution was calcium chloride with a 100 mM concentration. Average currents in response to 2V pulses were: 0.96+/−0.05, 0.68+/−0.02, 0.46+/−0.01 to for saline alone, 0.5× Heparin or 5× Heparin respectively. As demonstrated by FIG. 5, the microfluidic cartridge is capable of discriminating heparin solutions of different concentrations using a $Ca^{2+}$ reference sample because each solution generates a significantly different current in the microfluidic cartridge.

Example 3

The identity and concentration of some drugs can be detected by measuring changes in pH. For example, morphine is a natural base. Morphine increases the hydroxide ion ($OH^-$) concentration in aqueous solutions. Using water as a reference solution produces measurable changes in pH upon mixing in a microfluidic channel. pH changes in proportion to the concentration of morphine.

In order to detect pH changes, a set of pH-sensing electrodes were positioned in the microfluidic channel (Stanton J W, *Design and fabrication of a microfluidic electrochemical pH-stat*, Master's Thesis, Case Western Reserve University, 2010). The pH-sensing electrodes comprise a thin metal film (palladium or iridium) with an oxide layer (palladium or iridium oxide) thermally grown on the surface. Changes in pH were detected as a change in voltage measured by the sensing electrodes.

The use of headings and sections in the application is not meant to limit the invention; each section can apply to any aspect, embodiment, or feature of the invention.

Throughout the application, where compositions are described as having, including, or comprising specific components, or where processes are described as having, including or comprising specific process steps, it is contemplated that compositions of the present teachings also consist essentially of, or consist of, the recited components, and that the processes of the present teachings also consist essentially of, or consist of, the recited process steps.

In the application, where an element or component is said to be included in and/or selected from a list of recited elements or components, it should be understood that the element or component can be any one of the recited elements or components and can be selected from a group consisting of two or more of the recited elements or components.

It should be understood that the order of steps or order for performing certain actions is immaterial so long as the present teachings remain operable. Moreover, two or more steps or actions may be conducted simultaneously.

Where a range or list of values is provided, each intervening value between the upper and lower limits of that range or list of values is individually contemplated and is encompassed within the invention as if each value were specifically enumerated herein. In addition, smaller ranges between and including the upper and lower limits of a given range are contemplated and encompassed within the invention. The listing of exemplary values or ranges is not a disclaimer of other values or ranges between and including the upper and lower limits of a given range.

We claim:

1. A microfluidic device for use in a system comprising an intravenous delivery apparatus in fluid communication with the microfluidic device for providing an injectable test solution containing a test analyte to the microfluidic device, one or more intravenous lines with one or more ports to deliver the injectable test solution to the microfluidic device for analysis, a pump or pressure source to circulate the injectable test solution from one or more intravenous lines, and a reference solution, a valve in each of the intravenous lines for regulating flow of the injectable solution, and one or more controllers for operating the valves, the microfluidic device comprising:
   one or more test channels, each having a lumen;
   one or more reference solution channels in fluid communication with the one or more test channels;
   one or more sample channels in fluid communication with the one or more test channels with each sample channel also in fluid communication with the injectable test solution;
   a detector coupled to a plurality of sensors that are at least partially exposed within the lumen of the one or more test channels, the detector measuring at least one property of the test analyte;
   one or more ionic reference solution reservoirs in fluid communication with the one or more reference solution channels; and
   a processor that generates a response profile for the test analyte from said at least one measurement of a property, compares the generated profile to a known response profile for a specified analyte, estimates a likelihood that the generated profile and known response profile match within an acceptable range and generates an error signal when the likelihood of a match falls outside the acceptable range;
   wherein the response profile is generated by applying voltage pulses as the stimulus to the test analyte at one or more locations along the test channels, and
   wherein measuring the response to the stimulus received by the detector comprises measuring current resulting from the voltage pulses.

2. The microfluidic device of claim 1, wherein the detector measures at least one of electrochemical, chemical, physical, biological, biochemical, thermal and optical properties of the test analyte.

3. The microfluidic device of claim 1, wherein, when the processor outputs the error signal to the one or more controllers, the valve controlling flow of the injectable test solution is closed by the one or more controllers.

4. The microfluidic device of claim 1, further comprising a communication link to an alarm activated by the error signal.

5. The microfluidic device of claim 1, wherein information collected by the system by the processor is transmitted via an output interface.

6. The microfluidic device of claim 1, wherein the system further comprises an infusion pump that controls a flow rate of the injectable test solution, and wherein the flow rate is controlled by the processor communicating with the pump, based on the measured properties of the test analyte.

* * * * *